United States Patent [19]
Zadini et al.

[11] Patent Number: 5,466,221
[45] Date of Patent: Nov. 14, 1995

[54] PERCUTANEOUS CARDIAC PUMP FOR CARDIOPULMONARY RESUSCITATION

[76] Inventors: Filiberto P. Zadini, 16814 Rayen St., North Hills, Calif. 91343; Giorgio C. Zadini, 2237 Hilltop La., Camarillo, Calif. 93012

[21] Appl. No.: 924,301

[22] Filed: Aug. 3, 1992

[51] Int. Cl.$^6$ ................................................. A61M 29/00
[52] U.S. Cl. ................................. 604/96; 604/98; 606/192
[58] Field of Search ........................... 604/96, 97, 98, 604/104, 107; 606/191, 192, 194

[56] References Cited

U.S. PATENT DOCUMENTS

| | | | |
|---|---|---|---|
| 3,496,932 | 2/1970 | Prisk et al. | 604/272 X |
| 4,439,185 | 3/1984 | Lundquist | 604/97 |
| 4,940,459 | 7/1990 | Noce | 604/98 |
| 5,084,060 | 1/1992 | Freund et al. | 606/194 X |

*Primary Examiner*—Sam Rimell

[57] ABSTRACT

A method and apparatus for cardiac resuscitation comprising an expandable member placeable inside the chest cavity adjacent to the heart and means for periodically displacing said expandable member by applying and releasing pressure to it via a rigid stem, so to alternately compress and decompress the heart and including numerous safety mechanisms to prevent injury to the intrathoracic organs and mishaps.

63 Claims, 18 Drawing Sheets

5,466,221

PERCUTANEOUS CARDIAC PUMP FOR CARDIOPULMONARY RESUSCITATION

BACKGROUND

1. Field of Invention

This invention relates to methods and apparatus for cardiopulmonary resuscitation and is particularly directed to improved methods and apparatus for performing direct heart massage.

2. Prior Art

In order to resuscitate a patient victim of a cardiac arrest, it is necessary to provide an adequate artificial circulation of oxygenated blood to the vital organs by reestablishing the pumping function of the heart at values as close as possible to the physiological prearrest condition. Such a cardiac pumping function must be instituted at the earliest possible stage. It is documented that a cardiac arrest results in irreversible brain death if a sufficient blood flow is not reestablished within a critical period of time from the moment of the cardiac arrest. Such a period of time is measured ranging between four and six minutes.

In order to reestablish the pumping function of the heart, two methods of cardiopulmonary resuscitation have been used heretofore: external or closed cardiac massage, and internal or open cardiac massage. Closed cardiac massage consists of applying pressure on the anterior chest wall and alternately releasing such pressure. In the vast majority of cases, closed chest compressions produce a severe low flow state (Raymond E. Jackson: Basic Cardiopulmonary Resuscitation. Emergency Medicine, American College of Emergency Physicians). Open chest cardiopulmonary resuscitation improves hemodynamics, resuscitation and the chance of surviving cardiac arrest. Cerebral blood flow achieved with open chest techniques has been shown to be near normal physiological values. There are several case reports of patients who have been resuscitated with direct cardiac massage when attempts with closed chest cardiopulmonary resuscitation have been unsuccessful (Advanced Cardiac Life Support Textbook, American Heart Association, page 42). However, few physicians today are skilled in the technique of direct cardiac massage. Since most cardiac arrests occur outside of a hospital and since most patients cannot be brought to a facility where a thoracotomy and direct cardiac massage can be performed in less that 15 minutes of total arrest time, the applicability of direct cardiac massage has been limited (ACLS textbook, page 42). In addition to that, this technique is often characterized by many physicians as a rather grossly traumatic procedure, often seen as a desperate terminal attempt to resuscitate an arrested heart.

The aforementioned drawbacks of the two prior art techniques of heart massage have been recognized by Prisk and Johnson, who proposed a new method and apparatus for which they obtained a patent (U.S. Pat. No. 3,496,932, issued Feb. 24, 1970). The method and apparatus described by Prisk and Johnson includes an inflatable bladder, insertable through the subxyphoideal region into a space between the sternum and the heart via a trocar-cannula assembly. In order to accommodate the inflatable bladder and its stem, the sharp three-sided tip of the trocar must have a comparably large diameter, as illustrated in FIG. 4 of the Prisk and Johnson patent. However, the larger the sharp three-sided trocar tip, the more likely are injuries to the heart, coronaries or surrounding organs. In addition to the risk inherent in the size of the sharp tip of the trocar, the blind advancement of a trocar with a sharp tip in the thoracic cavity has been proposed by Prisk and Johnson. Such blind advancement carries extremely high risk of puncturing and/or lacerating the heart, coronary vessels or the surrounding structures, with devastating consequences. Prisk and Johnson's proposed position of blindly inserting the trocar between the sternum and the pericardial sac is, indeed, an extremely risky procedure; this space being very narrow, while it is virtually impossible to insert the trocar into the other designated position, i.e. within the pericardial sac (This space being only virtual, since the visceral and parietal pericardium are in contact, separated only by a thin film of pericardial fluid). Furthermore, the device proposed by Prisk and Johnson lacks any mechanism for locating the position of the sharp tip of the trocar and lacks any safety mechanisms to prevent or avoid injuries, such as puncturing of the heart or coronary vessels. Moreover, an inflatable bladder with a laterally flexible stem, as proposed by Prisk and Johnson, lacks the required stability for maintaining its central position to effectively compress the heart. Also, the proposed inflatable-deflatable bladder has no guidance, thus lacking the ability to properly impress direction of the compressions toward the vertebral column, allowing the heart to be displaced during the phase of compression laterally to the column, and not maintaining the heart in position between the vertebral column and the sternum, as required for effective pumping and resulting in ineffective compression of the heart. Given the individual variability in the size and depth of the thoracic cage, the device of Prisk and Johnson is inadequate in that it has no means to adapt to the various depths of the thoracic cavity and ignores the variability in the distance between the sternum and the vertebral column. Finally, the method of insertion of the Prisk and Johnson bladder is a multistep manual procedure, which is necessarily time-consuming and conflicts with the need for a rapid institution of cardiopulmonary resuscitation. Thus, none of the prior art methods and apparatus for cardiac pulmonary resuscitation have been entirely satisfactory.

BRIEF SUMMARY AND OBJECTS OF INVENTION

The disadvantages of the device of Prisk and Johnson, as well as those of closed and open cardiac massage, are overcome with the present invention and an improved method and apparatus for performing cardiopulmonary resuscitation is provided which permits direct cardiac massage without the risks inherent in massive opening of the thoracic cavity, as required in performing a thoracotomy.

It is a general object of our invention to provide a method and apparatus for cardiac massage which combines the hemodynamic effectiveness of direct heart massage with the rapidity of institution of closed heart massage, thus satisfying the two fundamental conditions required to restitute a human being to life and intact mental functions. Special attention was paid to the construction of a device which offers a satisfactory degree of safety in every phase of its operation. A safe device positively effects its effectiveness and its rapidity of application and, therefore, its usefulness.

More specifically, it is a main object of this invention to provide a heart assisting device which is hemodynamically effective in providing coronary arteries, cerebral arteries and systemic circulation with sufficient blood flow. In order to achieve hemodynamic effectiveness, the method of the present invention calls for insertion through the chest wall, in a designated area in front of the heart, of an expandable member such as an inflatable balloon via a blunt stem. The expandable member, fixed to the intrathoracic end of the blunt stem, is inserted via a rigid stem with a blunt tip through the thickness of the chest wall into the chest cavity adjacent to the heart. The expandable member is then expanded, and while it is maintained expanded, a mechanical force is then periodically applied to the extrathoracic end of the stem, causing the expandable member to alternately compress the heart against the thoracic spine and releasing such compression to effect pumping of the heart and generate artificial circulation. The stem also serves the purpose of guiding the direction of the expandable member as it moves. We are convinced that the device of the present invention grants hemodynamic effectiveness because the direction of compression is guided and the depth of compression and rate of pumping are adjustable.

It is also an object of the present invention to make the installation of a heart assisting device inside the chest cavity an extremely rapid operation. To accomplish such rapid installation, the device is constructed in such a way that its implementation does not require specialized medical knowledge and, consequently, the device of the present invention may be applied by semi-skilled persons, such as paramedics and the like, which would ultimately effect its rapidity of installation and, hence, its usefulness. Moreover, the device of the present invention can safely be applied in a hospital or in the field, out of a hospital setting. This feature of rapid and easy installation is achieved by the ability of applying the device to an easily accessible and easily identifiable designated area either on the anterior chest wall or on the subxyphoideal region, by the use of a small gauge stem and by the automation of most of the operations of the device, except those controlling the depth and rate of compression, which are preferably left to the discretion of the operator of the device to permit such variations as are desirable to obtain optimal blood flow.

An additional object of the present invention is to construct a device which is as safe as possible in every phase of its operation. Such safety is achieved by a number of features, such as:

1) Use of a disposable sterile unit as that part the device which will enter the chest cavity to prevent transmission of infections.
2) Use of a blunt stem to prevent accidental punctures.
3) Use of an inserting mechanism for the inflatable expandable member which grants controlled insertion of the tip of the stem into the chest cavity through the chest wall and also grants control of the angle of insertion of the stem so that the inflatable expandable member is properly directed in front of the heart to ensure that compression of the heart is directed against the thoracic spine.
4) Use of a feature which grants automatic arrest the stem advancement into the chest wall, as soon as the tip of the stem has entered the chest cavity, to prevent possible damage to the heart during the insertion of the stem.
5) Use of an automatic and rapid sequence of preparatory steps leading to the inflation of the expandable member in front of the heart.

In general the automation of the preparatory steps should be regarded as a features provided for the purpose of safety, besides rapidity of implementation, because such automation tends eliminate the possibility of afflicting the operation with human errors, a calamitous inconvenience, but the most likely to occur in a highly rushed situation, such as a cardiac resuscitation attempt.

It is also an object of the present invention to provide an alternative method of safe insertion of a expandable member within the chest cavity; an automatically intervening alternative, in case of malfunctioning of part of the device; arranging for arrest of the operations, easy and rapid extraction of the defective device, and untroubled reinsertion of a replacement device.

These and other objects and features of the present invention will be apparent from the following detailed description, taken with reference to the figures of the accompanying drawings.

DETAILED DESCRIPTION OF THE INVENTION

In that form of the present invention chosen for purposes of illustration in FIGS. 1–10, a percutaneous cardiac pump, indicated generally at 1, is shown with the actuating mechanism shown in the normal rest position. As best seen in FIGS. 3A and 3B, the cardiac pump 1 is composed of three main components: a support case, indicated generally at 2; the stem member, or main unit, or stem unit, all indicated generally at 100; and an intermediate member, indicated generally at 300, interposed between the stem member 100 and the support case 2.

Figure 1:
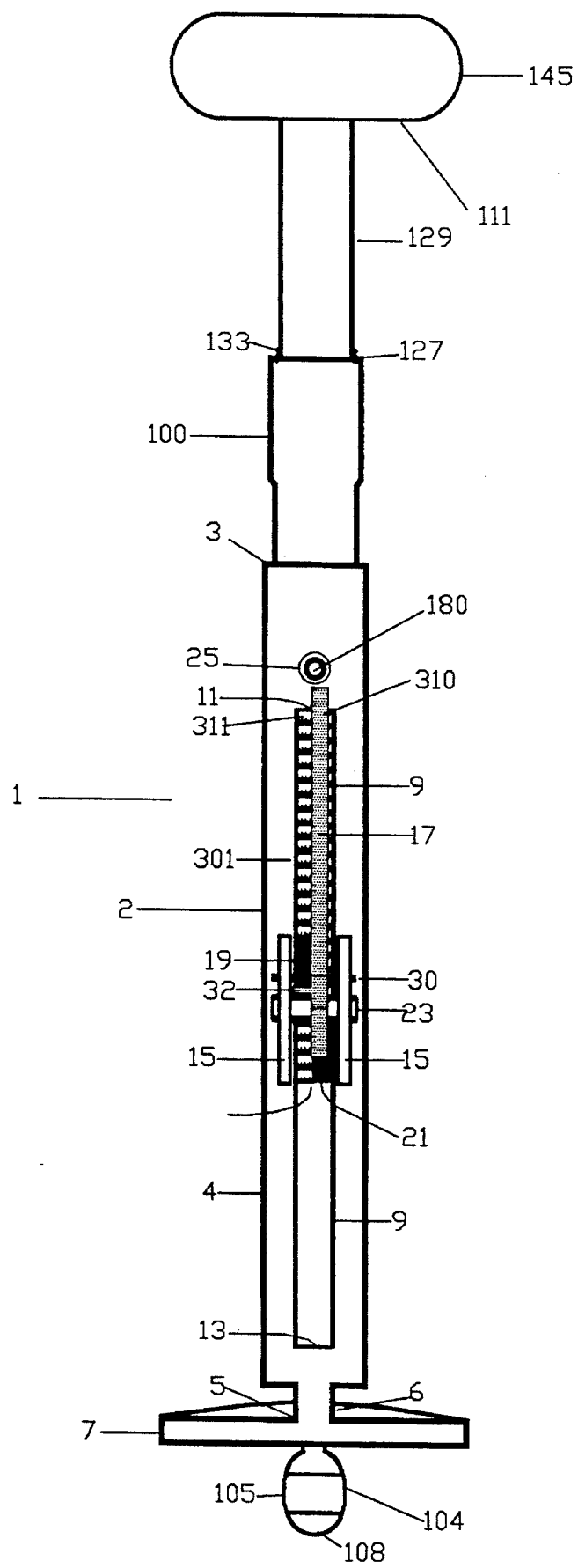
FIG. 1 is a front view of a cardiac pump embodying the present invention.
Figure 2:
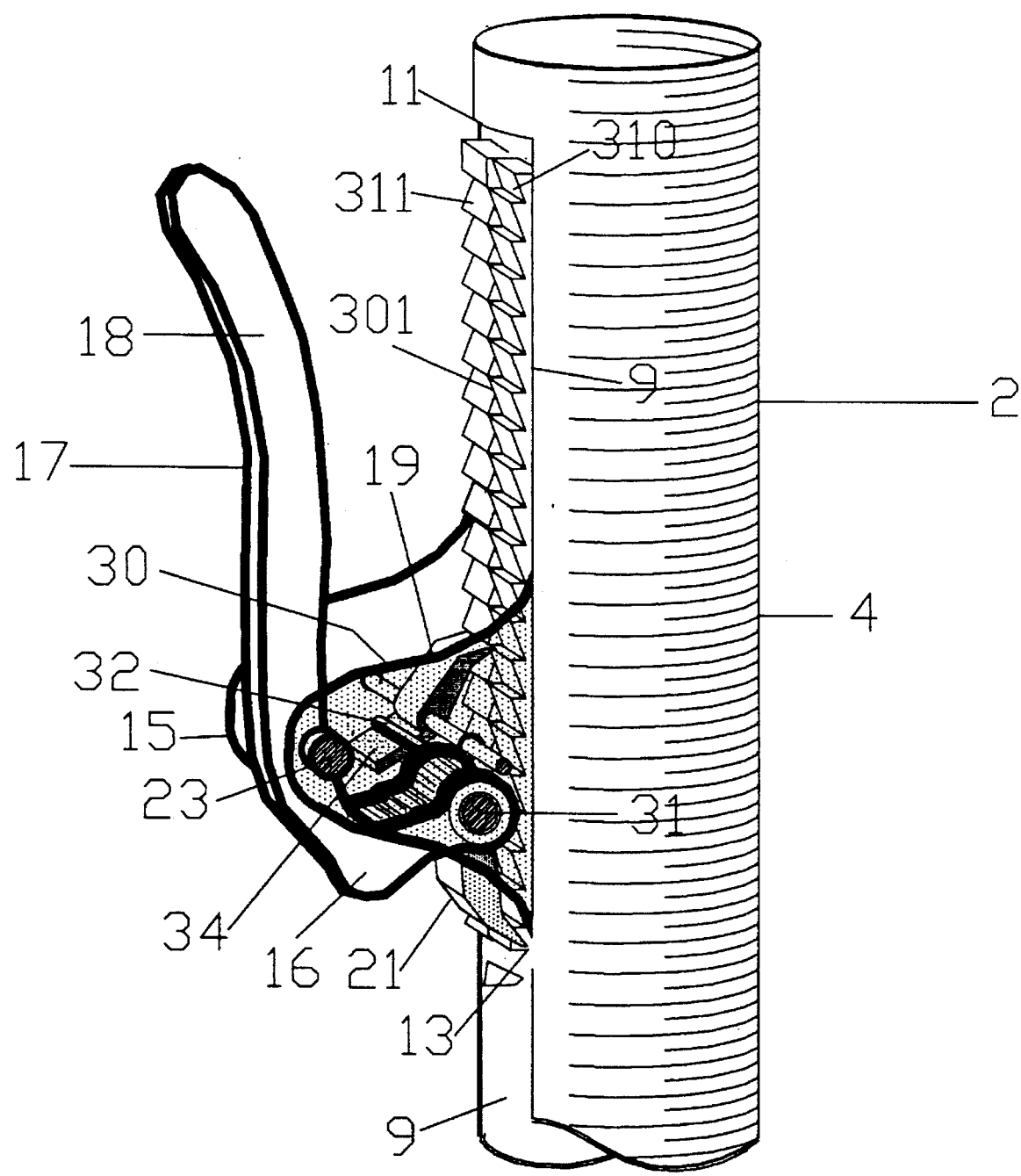
FIG. 2 is tridimensional view of the lever-double rack mechanism of advancement, shown in front view in FIG. 1.
Figure 3A:
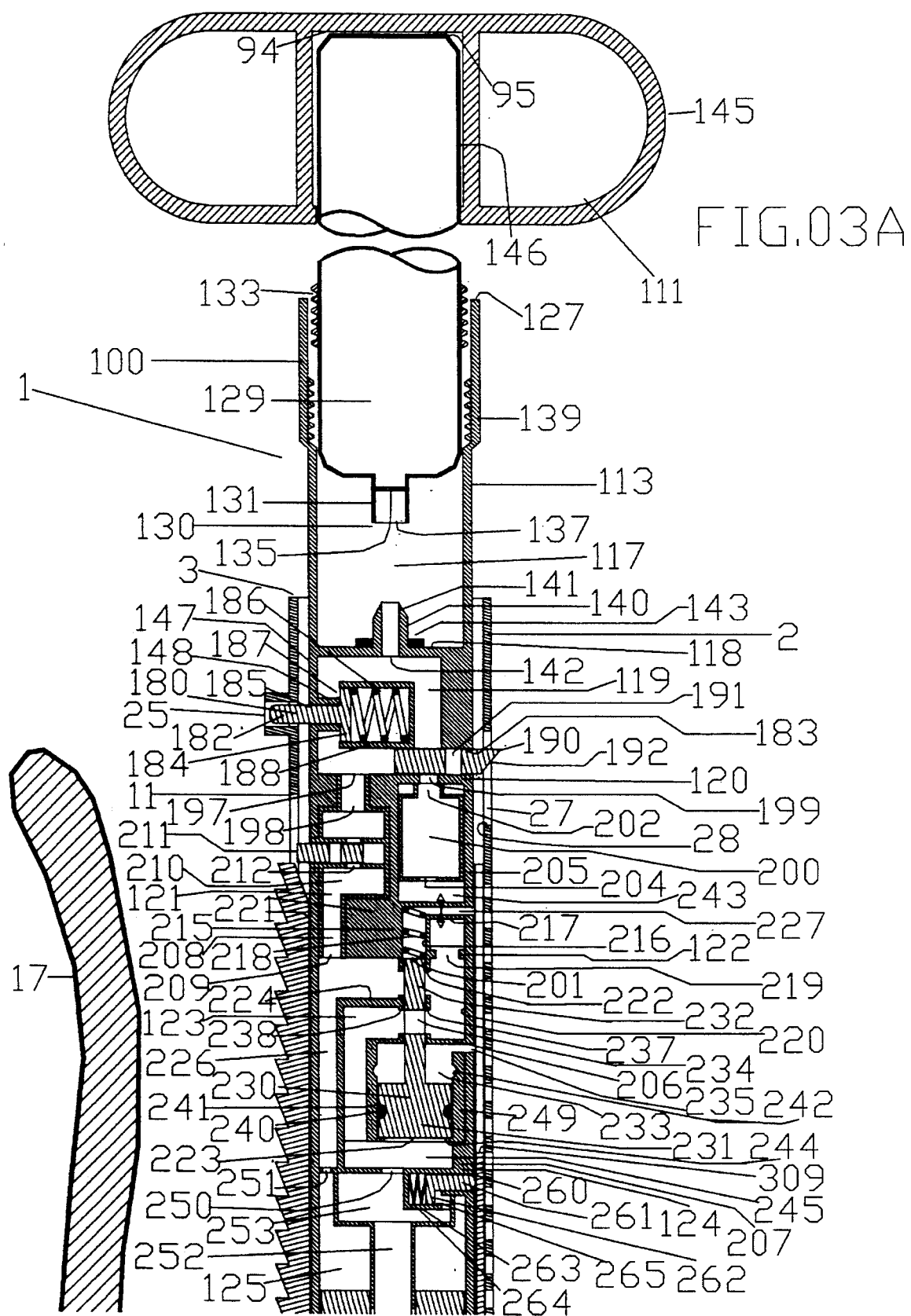
FIGS. 3A and 3B are vertical sections, respectively through the upper portion and lower portion of the cardiac pump of FIG. 1, showing the cardiac pump is its normal rest position.
Figure 3B:
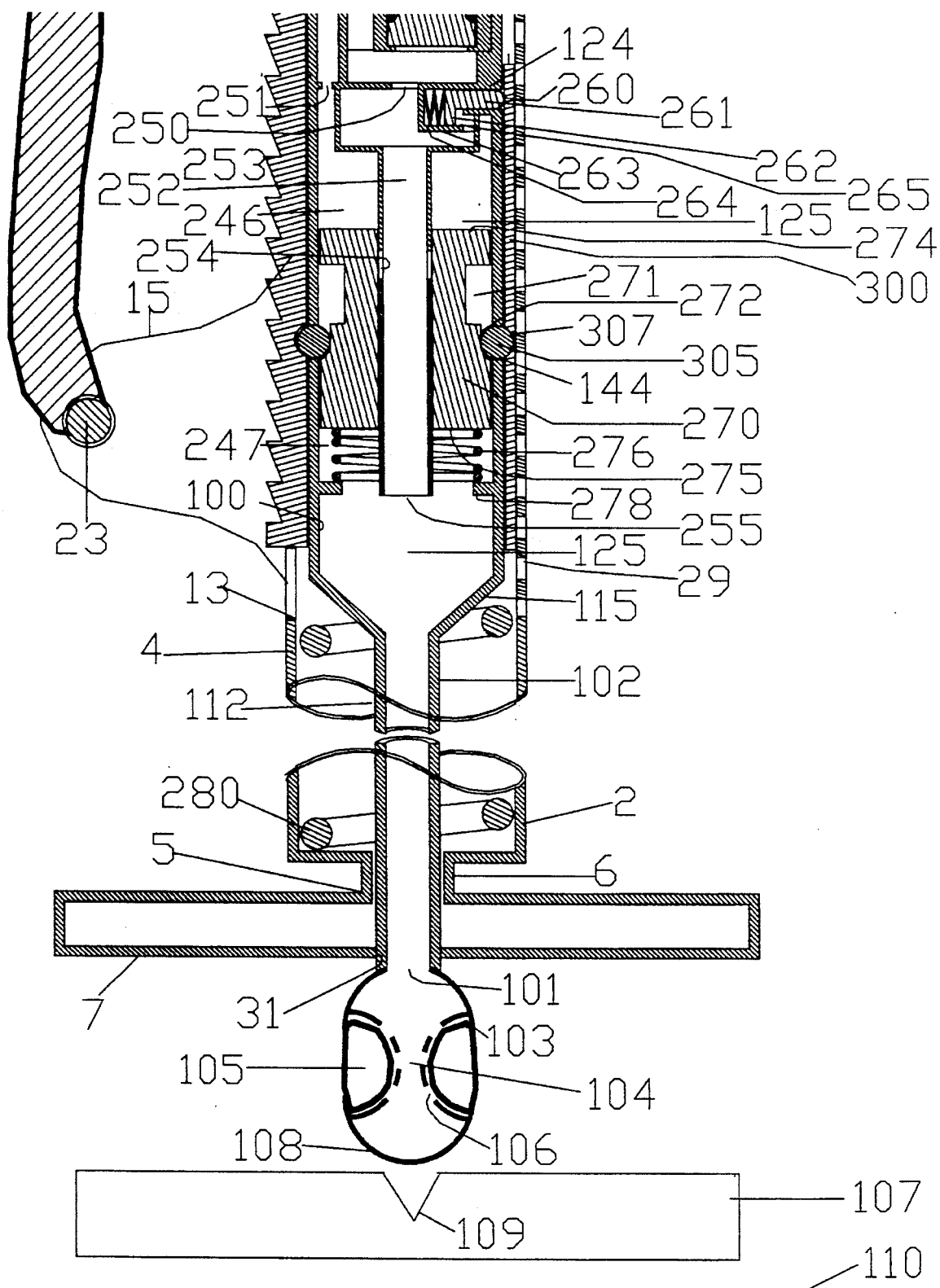

The support case 2 is hollow and is of generally tubular, cylindrical shape having an open proximal end 3, a body 4 and a distal end 5, including a narrow neck 6 and a flat, circular base 7. The base 7 is preferably formed of transparent material to enable the operator to better visualize the actual position of the pump 1 on the anterior chest of the patient. Also, base 7 is formed with a central opening 31 to allow passage therethrough of stem 102 of the stem member 100, as seen in FIGS. 1 and 3B and more fully described below. The body 4 of the support case 2 has a longitudinal slit 9 extending from its proximal end 11 to a distal end 13. As best seen in FIG. 2, two parallel ears 15 are attached to the body 4 of the support case 2 and protrude outwardly adjacent each side of the slit 9. Lever 17, with dogs 19 and 21, is interposed between the ears 15 and is pivotally secured to the ears 15 by suitable means, such as pin 23, to form a fulcrum for the lever 17. A double rack 301 is mounted on the intermediate member 300 and projects through the slit 9 for engagement by dogs 19 and 21 of the lever 17. Dog 21 is pivotally secured to lever 17 by pin 31, while dog 19 with its tail 34 is pivotally secured to ears 15 via pin 30. Displacing rod 32, which protrudes from one end of pin 31, seats on tail 34 of dog 19.

The intermediate member 300 is generally tubular and is interposed between the support case 2 and the stem member 100. As noted above, the double rack 301 is mounted on the intermediate unit 300 and projects through slit 9 of the support case 2. As best seen in FIG. 2, the double rack 301 comprises a first rack 310, having teeth 8 oriented downward, and a second rack 311, having teeth 11 oriented upward. The intermediate member 300 has a slit 309, seen on the right side of FIG. 3A. In the starting or rest position, the lower end of the slit 309 is positioned slightly above and in line with pin 260 of the stem member 100. Intermediate member 300 is locked to the stem member 100, in the rest position, by balls 305 which seat in receptacles 307 of the intermediate unit 300.

Figure 4:
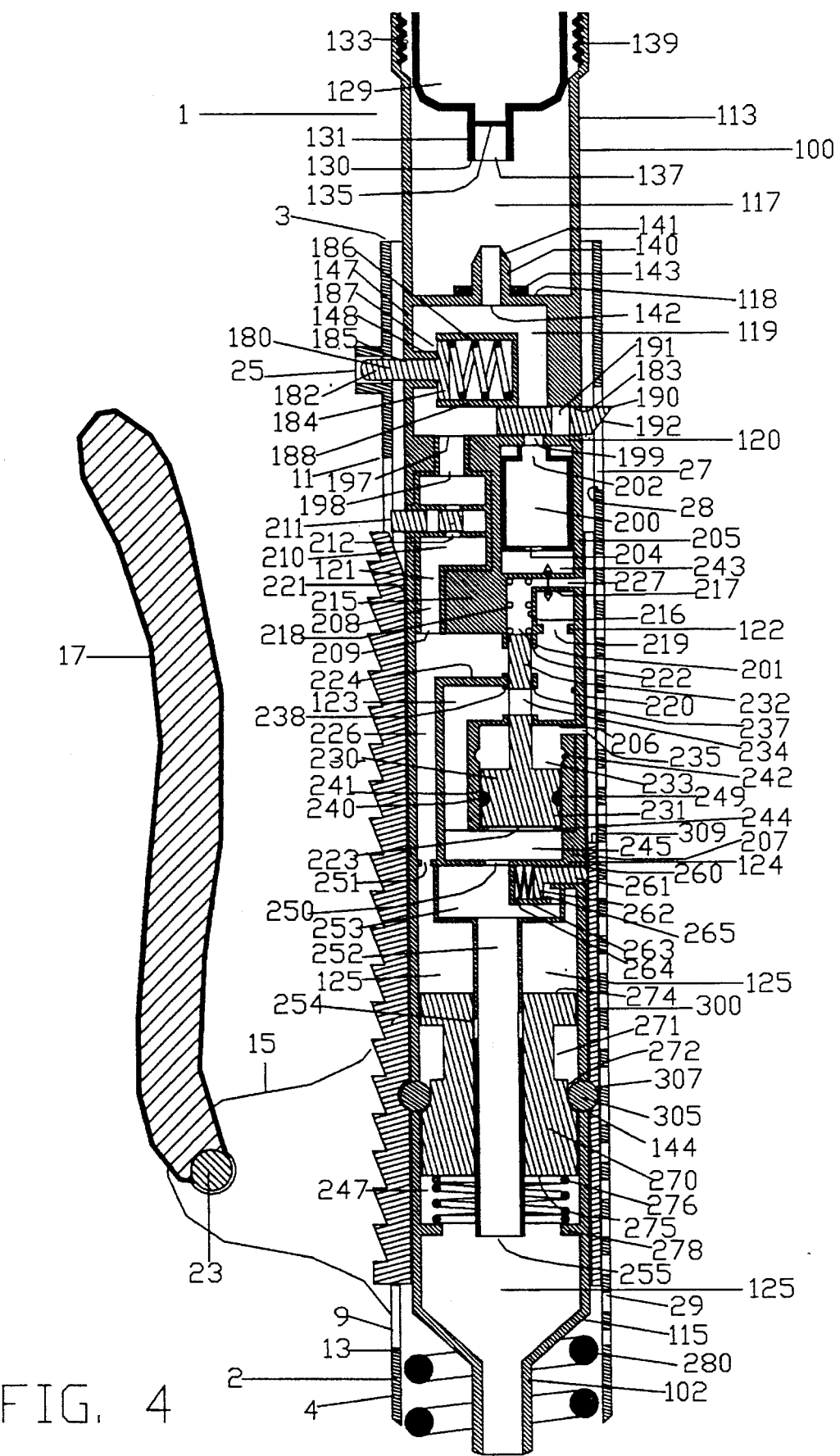
FIG. 4 is an enlarged detail view of the central portion of the device as shown in FIGS. 3A and 3B.
Figure 5:
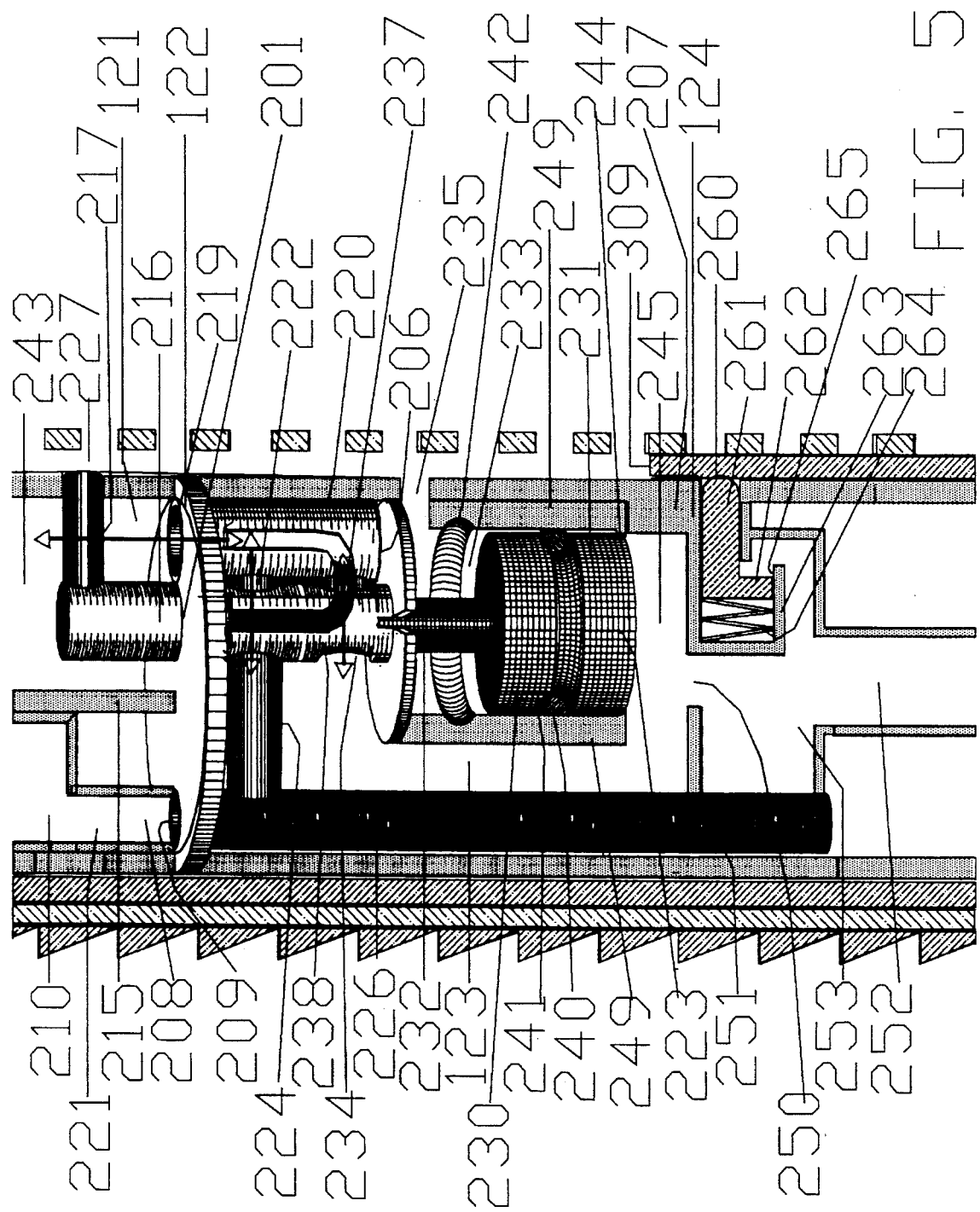
FIG. 5 is a tridimensional representation of a portion of the stem member of the cardiac pump of FIG. 1.
Figure 6:
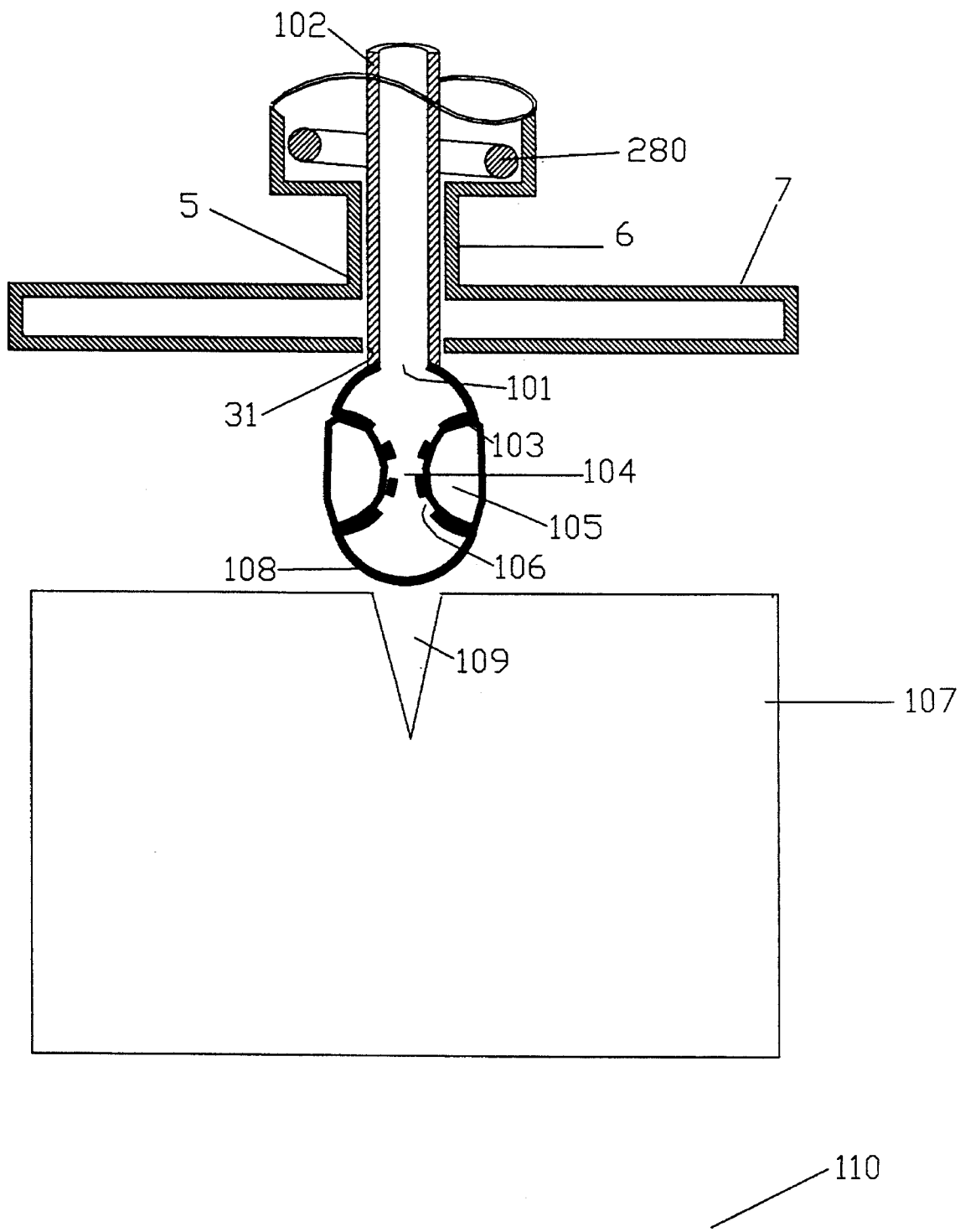
FIG. 6 is an enlarged vertical section of the lower tip of the cardiac pump of FIG. 1.

The stem member 100 is located centrally within the support member 2 and the intermediate member 300. The stem member 100 is a rigid hollow cylinder composed of three parts: handle 111, body 113 and stem 102. As noted above, stem 102 protrudes from the distal end 115 of body 113 and projects through opening 31 in the base 7 of the support member 2. At the upper end of the stem member 100 is a generally T-shaped handle 111, having a transverse bar 145 mounted on the upper end of an elongated, cylindrical gas-filled or fluid-filled bottle 129. The bottle 129 carries an externally threaded portion, as seen at 133 in FIG. 3A, and contains a quantity of compressed gas such as air, or fluid under pressure, which is retained within bottle 129 by a suitable seal 135 mounted in nozzle 131 of the bottle 129. As best shown in FIG. 4, the body 113 comprises five chambers 117, 119, 121, 123 and 125. Chamber 117 is located adjacent the upper end of the body 113 and has an open end 127 which receives the nozzle 131 of the air bottle 129 and has a diaphragm 118 defining the boundary between chamber 117 and chamber 119. Chamber 117 also has an internally threaded portion 139, which is matable with the external threads 133 of the air bottle 129. Also within chamber 117, a hollow needle 140, having a needle tip 141, is mounted on the diaphragm 118, as by gasket 143. Chamber 119 extends between diaphragm 118, at its upper end, and diaphragm 120, at its lower end. Within the chamber 119, is a pin 180 having a pin shaft 182 projecting laterally from pin head 184, which is slideably mounted within a cylindrical pin case 188 and is urged by suitable means, such as spring 186 mounted within the pin case 188, to project through opening 25 of the support case 2, when the cardiac pump 1 is in the rest position. As best seen in FIG. 4, the pin shaft 182 projects, in air-tight manner, through window 185 of sidewall 147 of chamber 119. Diaphragm 118 is formed with a central opening 142 which communicates with the interior of hollow needle 141. Also within chamber 119, below the pin case 188, a shutter 190 is mounted for lateral sliding movement through window 183 of the stem member 100 and window 27 of the support case 2. Shutter 190 has a downwardly and inwardly slanted outer end 192 and is provided with an opening 191 located eccentrically and extending vertically through the shutter 190. In the rest position, shutter 190 covers and seals opening 199 of lower diaphragm 120, while uncovering opening 197 of diaphragm 120. Within chamber 122, the opening 199 is connected to inlet 202 of pressure valve 200, while opening 197 communicates with inlet 198 of shut-off valve 210. Pressure valve 200 also has an outlet 204. Shut-off valve 210 also has an outlet 208 and contains a shutter 211, which controls passage of air through the outlet 208 and which is movable through opening 212 of shut-off valve 210 to project into slit 9 of the support case 2 above the upper end of the double rack 301. Diaphragm 122, as best seen in FIGS. 4 and 5, defines the boundary between chamber 121, above, and chamber 123, below, and is formed with opening 209, communicating with outlet 208 of shut-off valve 210, and with openings 201 and 219. Opening 201 is connected to pipe 216, which communicates with chamber 123, but projects above diaphragm 122, into space 243 below the pressure valve 200, and is connected to exit pipe 217, which exits through opening 227 of side wall 205 of chamber 121. Chamber 123 is defined by upper diaphragm 122 and lower diaphragm 124 and is best understood from FIGS. 3A, 4 and 5. As shown, a pipe 226 extends completely through chamber 123, between opening 209 in upper diaphragm 122 and opening 251 in lower diaphragm 124. Pipe 220 extends downward from opening 219 of upper diaphragm 122, parallel to pipe 216, and terminates at plate 206, which defines the upper end of piston chamber 233. A transverse opening 222 communicates the interior of pipe 216 with that of pipe 220. Similarly, transverse pipe 224 communicates the interior of pipe 216 with that of pipe 226. Below the transverse pipe 224, pipe 216 has a second transverse opening 237 communicating with the interior of pipe 220 and an additional transverse opening 238 which opens to into chamber 121. The piston chamber 233 is enclosed by a cylindrical wall 249 and has a piston 230 slideably retained therein. Piston 230 has a piston head 231 and a piston shaft 232, which extends slideably into the lower end of pipe 216. As seen in FIG. 4, a spring 218 is located within pipe 216, above the end of piston shaft 232, and bears against the end of piston shaft 232 to urge the piston 230 downward to seat against annular retainer 244. The piston shaft 232 is formed with a transverse opening 234 which, in the rest position, is aligned with opening 237 of pipe 220 and with transverse pipe 224, which communicates with pipe 226. Piston 230 is also formed with an annular recess 241, which seats piston ring 240. Also, the cylindrical wall 249 of the piston chamber 233 has an annular recess 242, formed adjacent the upper end thereof, which serves to receive piston ring 240 to releasably lock the piston 230 in its upper position, as more fully described below, and has a lateral opening 235 communicating with the exterior of the cardiac pump 1 above recess 242. Below piston 230, space 245 separates the lower surface 223 of piston 230 from lower diaphragm 124 of chamber 123. As noted above, diaphragm 124 has an opening 251, which receives pipe 226, and has a central opening 250 which communicates with the expanded proximal end 253 of pipe 252 in subjacent chamber 125. Chamber 125 extends between diaphragm 124, at the upper end, and the open lower end of body 113 of the stem member 100. Within the expanded upper end 253 of pipe 252 is a pin case 263, containing a pin 261, having a pin head 262, and having a spring 264 mounted within the pin case 263, behind the pin head 262, to normally urge the pin 261 laterally outward to project through opening 260 on the wall of the stem member 100 pressing against the wall of the intermediate member 300, just below slit 309 of intermediate member 300. Pipe 252 extends downwardly within chamber 125 and terminates at the level of flange 275, which serves as a seat for piston 270. Piston 270 is slideably mounted about pipe 252 and, in the rest position, is located to close transverse openings 254 of pipe 270. Piston 270 is formed with an annular recess 271 with a subjacent annular receptacle 272. In the rest position, balls 305 sit in window 144 of stem member 100 and are retained between receptacle 272 of piston 270 and receptacle 307 of the intermediate member 300 to releasably lock the stem member 100 to the intermediate member 300. Spring 276 is seated on flange 278 and serves to normally urge the piston 270 upward to cause receptacle 272 to retain the balls 305 in their "locked" position. As best seen in FIG. 3B, a large spring 280 is located within the lower end of the support case 2 and bears against the lower end 115 of the stem member 100 to urge the stem member 100 upward. As seen in FIGS. 3B and 6, an elongates hollow stem 102 extends downward from the lower end 115 of the stem member 110 and exits through opening 31 of the flat base 7 of the support case 2 to support a blunt end 104 of spheroid shape having a circular groove 103 which contains an expandable member such as balloon 105, which is folded when the cardiac pump 1 is in its rest position. The stem end, or stem tip, 104 is blunt in order to avoid injuries such as puncture wounds and lacerations to the intrathoracic organs. The relatively small size of the stem end meets little resistance from the chest wall structures that it has to transpass in order to reach the chest cavity, once a skin incision is done, as it will be described below. Stem 102 communicates with the interior of stem end 104 through opening 101 and communicates with balloon 105 through openings 106 within groove 103. Stem end 104 has a blunt end 108 and is generally in the form of a hollow dome. FIG. 6 also diagrammatically shows the anterior thoracic wall 107, with the skin incised at 109, together with the underlying chest cavity 110 containing the heart 69.

Figure 7:
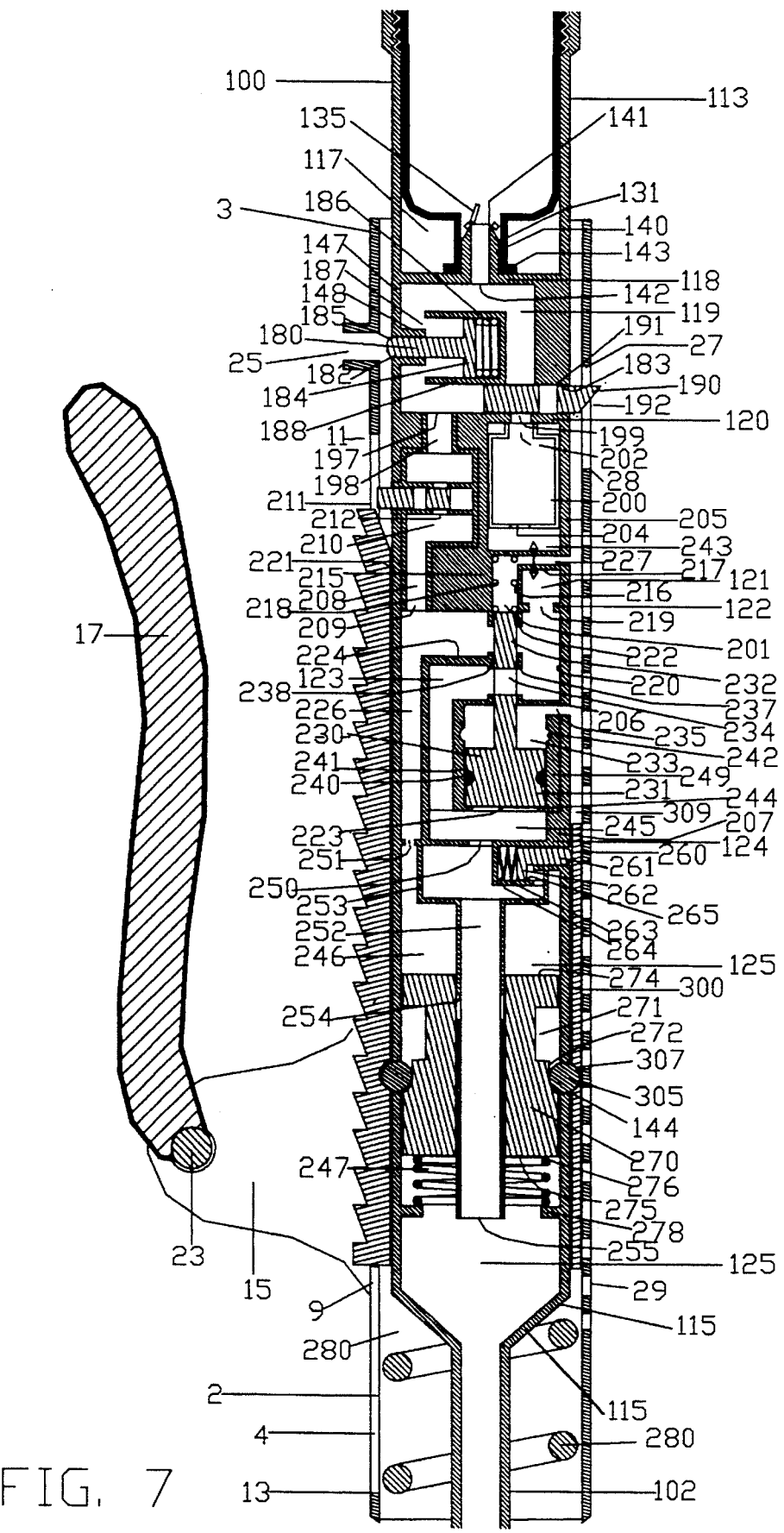
FIG. 7 is a view, similar to that of FIG. 4, showing the cardiac pump of FIG. 1 in its second stage of operation.

To apply the cardiac pump 1, the operator makes a small incision 109 in the patient's skin adjacent the 4th or 5th intercostal space along the left sternal border of the patient or in the subxyphoideal region. The skin incision is carried out with a suitable surgical instrument such a lancet, or surgical knife, preferably provided with an arrest to prevent deep penetration. After appropriate sterilization, the cardiac pump 1 is placed on the patient's chest with the tip 104 of stem 102 inserted into the incision 109. When this is done, the stem tip 104 will be partially buried under the patient's skin within the thoracic wall 107, but will not have entered the chest cavity 110, and base 7 of the support case 2 will be seated on the appropriate area of the chest wall 107. Next, the operator rotates handle bar 145, causing threads 133 of the air bottle 129 to engage threads 139 of upper chamber 117 of the stem member 100, an drawing the adapter 131 of the air bottle 129 toward needle 141 until the needle tip 140 of needle 141 enters the adapter 131 and pierces seal 135, as seen in FIG. 7, allowing the compressed air contained within the air bottle 129 to flow through needle 141 and opening 142 in diaphragm 118 into chamber 119 of the stem member 100. The operator continues to screw the handle 145 until a tight seal is obtained by the adapter edges 130 pressing firmly against gasket 143. As the compressed air enters chamber 119, the air pressure will bear against pin head 187 of pin 180, driving pin 180 medially against spring 186 to remove pin shaft 182 from projecting through window 25 of support case 2 and, thus, unlocking the main unit 100 from the support case 2.

If the air pressure is insufficient, or if a leak allows the air to escape, pin shaft 182 of pin 180 will not disengage from window 25 and the stem member 100 will remain locked to the support case 2, thereby preventing further operation of the cardiac pump 1.

If the air pressure is adequate to actuate pin 180 and, hence, to unlock the stem member 100 from the support case 2, the operator will repeatedly press lever 17, causing the dogs 19 and 21 to act on the racks 311 and 310, respectively, and to displace the double rack 301 downward. More precisely, a displacement of handle 18 of lever 17 toward racks 301 will cause a downward movement of dog 21 pivoted on pin 31 of arm 16 of lever 17: the downward movement of dog 21 which is engaged in rack 310, with upwardly oriented teeth, will result in a downward displacement of rack 310. While arm 16 of lever 17 moves downward, pin 32, protruding from one end of pin 31 will displace tail 34 of dog 19 toward rack 311, releasing dog 19 from rack 311, with downwardly oriented teeth, just before downward movement of rack 310 is initiated, and locking rack 311 immediately after advancement of rack 310. Advancement of rack 310 in turn will carry intermediate member 300 and stem member 100 downward, due to the interlocking performed by balls 305 sitting in windows 144 of the stem member 100 and in receptacle 307 of intermediate member 300. Balls 305 are retained in windows 144 and receptacle 307 by the annular receptacles 272 of piston 270, which is urged to its upward position by spring 276 acting between flange 278 of the stem member 100 and the lower surface 275 of piston 270.

As it can be understood from FIG. 7, after the intermediate member 300 and stem member 100 are advanced a predetermined length with respect to the support case 2, preferably about ½ centimeter, by the operator acting on the lever 17, shutter 190 will be displaced medially, due to the edge 28 of window 27 bearing against the slanted end 192 of shutter 190. This displacement of shutter 190 will permit the compressed air to enter pressure valve 200 by passing through opening 199 of diaphragm 120 and inlet 202 of the pressure valve 200. The compressed air will exit, through outlet 204 of pressure valve 200, at a preestablished pressure and will travel through opening 119 of diaphragm 122, connected pipe 220, opening 237, window 234 of piston 230, chamber 123, opening 250 of diaphragm 124, expanded end 253 of pipe 252, through pipe 252, space 247 below piston 270, through the elongated hollow stem 102 and opening 101 into tip 104 and will attempt to pass through openings 106 to inflate balloon 105. However, balloon 105 will be prevented from inflating due to the inextensibility of the surrounding chest wall structure 107. As a result, the air pressure within the pathway, just described, will quickly reach equilibrium with the pressure at outlet 204 of the pressure valve 200. As this occurs, the air pressure within this pathway will act upon the lower surface 223 of piston 230 and will force piston 230 to move upward, against the urging of spring 218, until piston ring 240 becomes seated in annular recess 242 of piston chamber 233, locking piston 230 against further upward movement and aligning opening 234 of the piston shaft 232 with window 222 of pipes 216 and 220. This movement of piston 230 and piston shaft 232 will close opening 237 and, hence, will force the compressed air from pressure valve 200 to flow through lateral pipe 224, vertical pipe 226, opening 251 of diaphragm 124 and into space 246 above piston 270. At this point, the air pressure in space 246, above piston 270, and in space 247, below piston 270 will be equal. Consequently, piston 270 will be urged into its upward position by the action of spring 276. Moreover, pressure valve 200 serves to regulate the air pressure below the pressure valve 200 and to assure that the air pressure in balloon 105 and in the various pathways between the balloon 105 and pressure valve 200 is less than the air pressure within the air bottle 129. This is a second safety feature and assures that the air pressure within the balloon 105 will be insufficient to cause disruption of the chest wall structure 107. The automatic arming of the cardiac pump 1 is now completed, within a few seconds of initiation of the operation, and the cardiac pump 1 is ready for further operation.

Figure 8A:
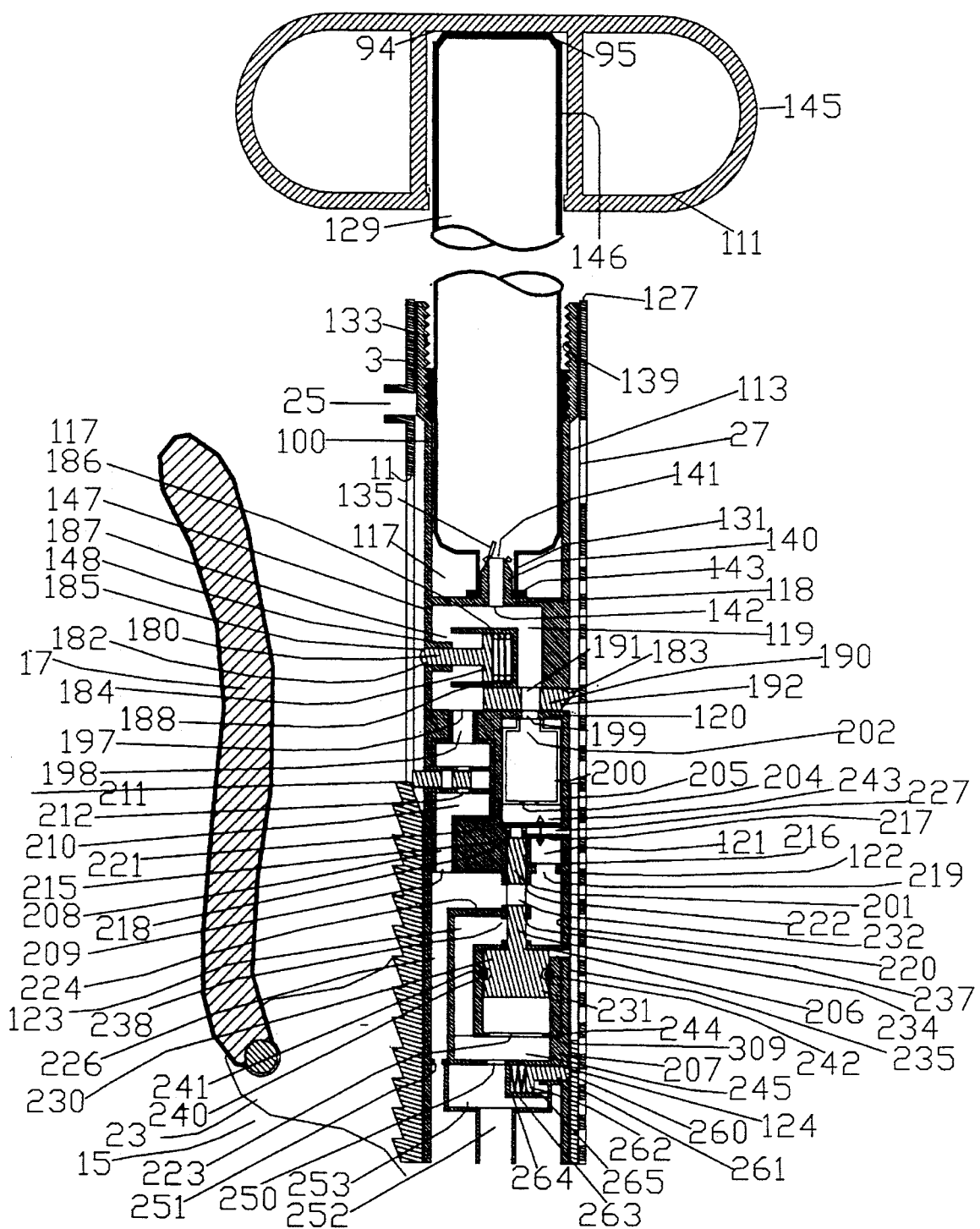
FIGS. 8A and 8B are views similar to the views, respectively, of FIGS. 3A and 3B, FIG 8B showing the stem tip of the cardiac pump of FIG. 1 at the instant it enters the patient's chest cavity.
Figure 8B:
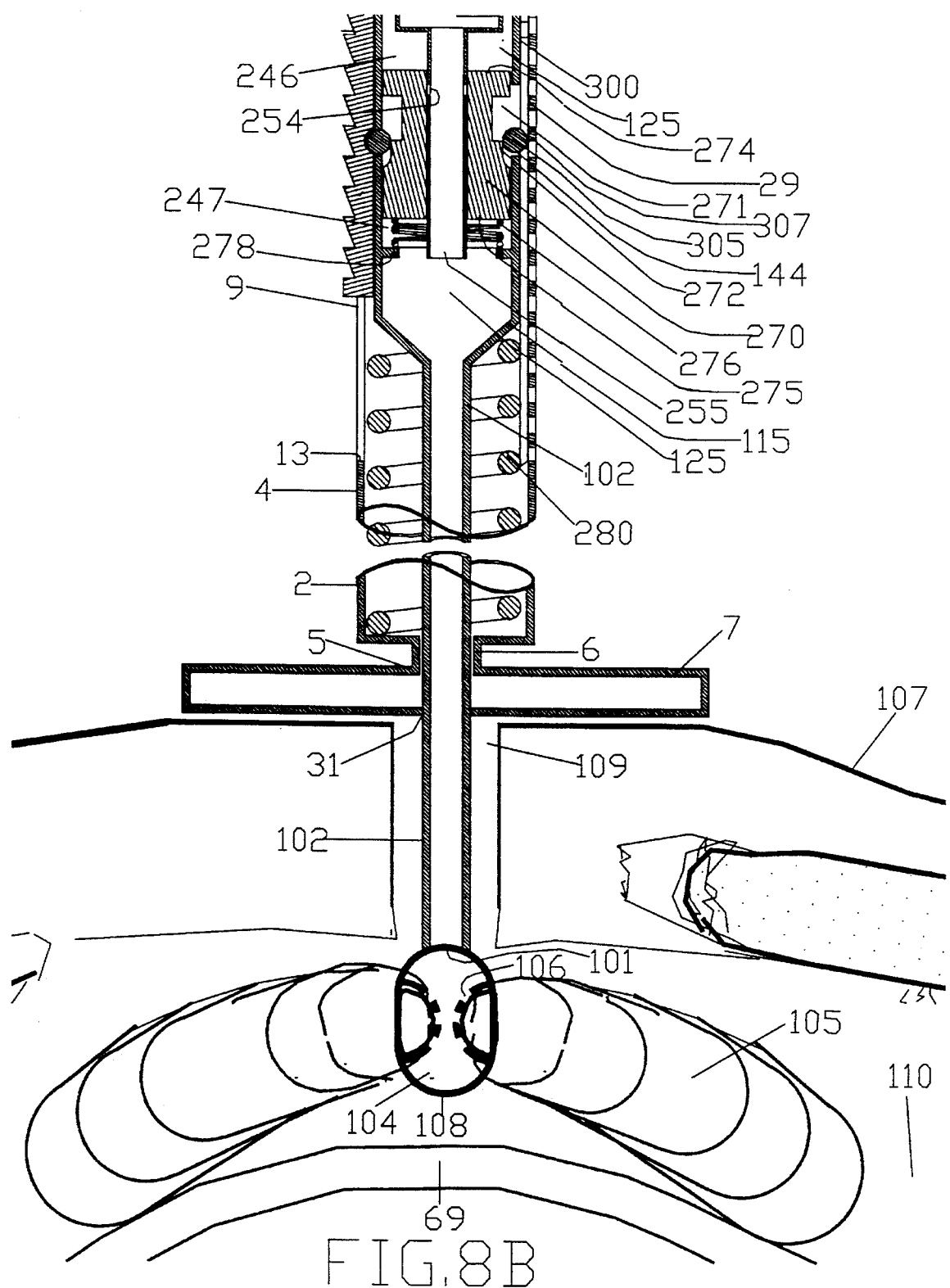

In the next stage of the operation, the operator continues actuating lever 17, causing further advancement of the stem tip 104 through the chest wall structure 107 toward the chest cavity 110. As seen in FIG. 8B, the instant that the stem tip 104 passes out of the chest wall structure 107 into the chest cavity 110, the balloon 105 will expand, due to the fact that the balloon 105 is no longer enclosed by the chest wall structure 107 and the compressed air within the stem 102 is able to pass through openings 106 into the balloon 105. The expansion of the balloon 105 will result in a pressure drop within space 247, below piston 270. Because piston 230 has been forced to its upward position, as described above, air can no longer flow through opening 234 of piston 230 to re-supply space 247. Consequently, the air pressure in space 246, above piston 270, will exceed the air pressure in space 247, below, piston 270, and will drive piston 270 downward, against the urging of spring 276. As piston 270 is driven downward toward flange 278, it will expose windows 254 of pipe 252, permitting air form space 246, above piston 270, to pass into pipe 252 and, thus, through stem 102 to further inflate the balloon 105.

Figure 9:
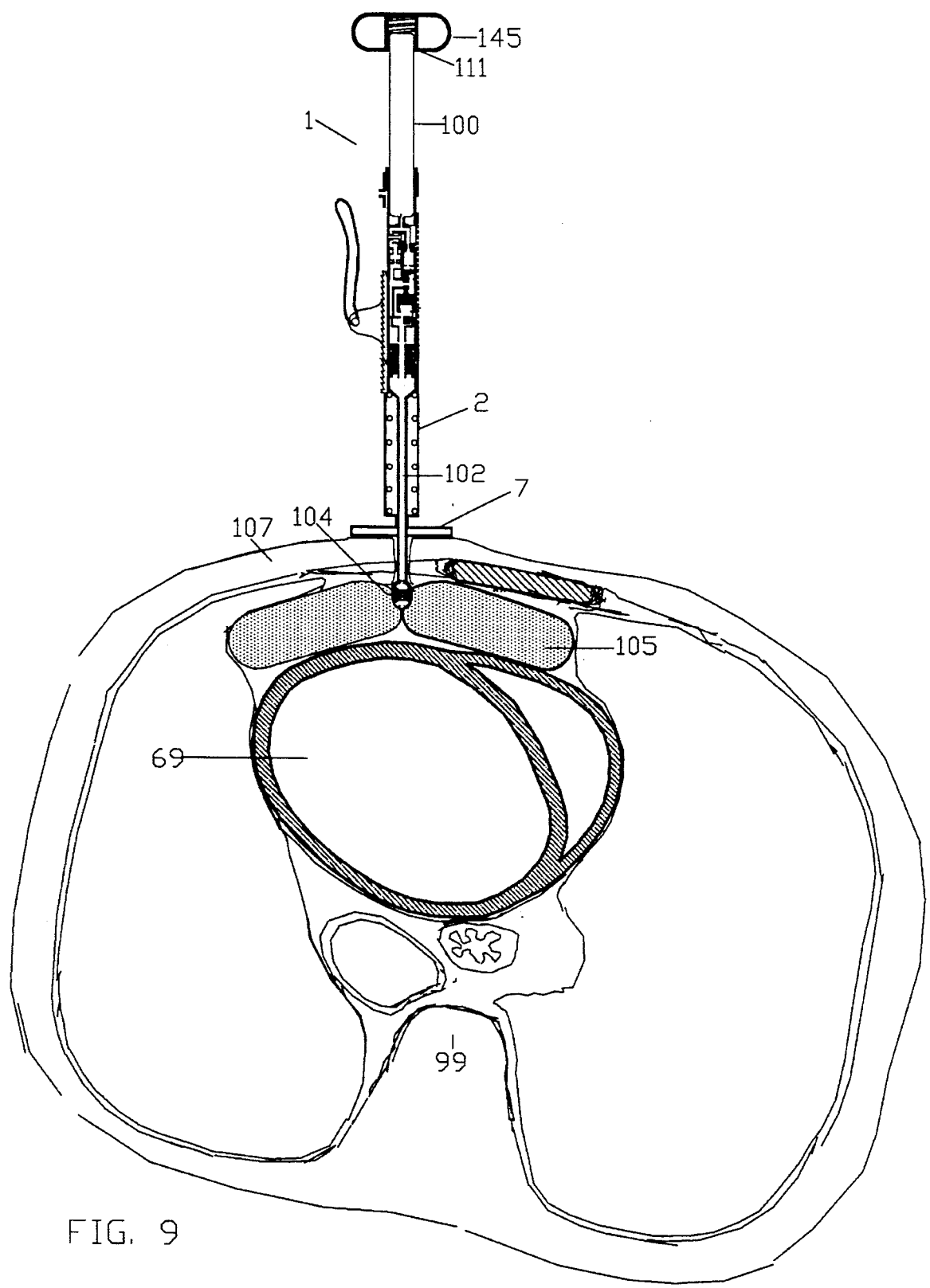
FIG. 9 is a view similar to the views of FIGS. 3A and 3B showing the stem tip of the cardiac pump of FIG. 1 with the expandable member fully inflated prior to compression of the heart.
Figure 10:
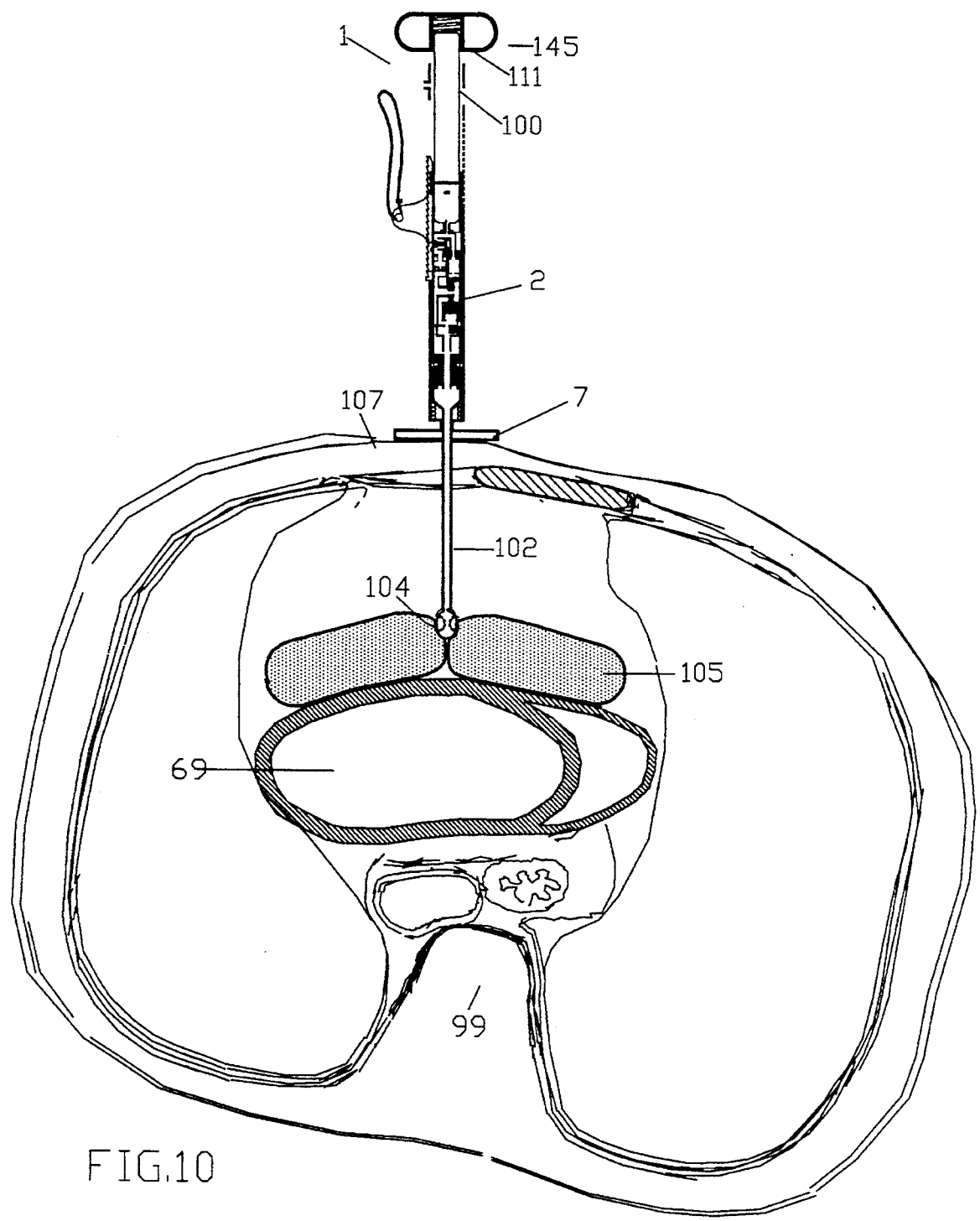
FIG. 10 is a view similar to that of FIG. 9 in a further stage showing the actual the compression of the heart against the vertebral column.

The forward movement of the piston 270 also causes balls 305 to be transferred from the recesses 272 into the larger recess 271 of piston 270, which allows the balls 305 to disengage from windows 144 of the stem member 100 and, thus, unlocks the stem member 100 from the intermediate member 300, which prevents lever 17 and double rack 301 from causing any further advancement of the tip 104 into the chest cavity 110. Simultaneous with the unlocking of the stem member 100 from the intermediate member 300, spring 280 acts between the distal end 5 of the support case 2 and the lower end 115 of the stem member 100, forcing the stem member 100 upward until spring 264 is able to drive pin 261 outwardly to project through opening 260 of stem member 100 and through slit 309 of the intermediate member 300 to engage to opening 29 of the support case 2 and, thus, to lock the stem member 100 to the support case 2. This serves to prevent accidental advancement of the stem 104 of the stem member 100 prior to full inflation of the balloon 105. Also, the unlocking of the stem member 100 from the intermediate member 300 renders lever 17 ineffective, which provides a tactile indication to the operator that the stem member 100 has been unlocked from the intermediate member 300 and is now locked to the support case 2. In response to this tactile signal, the operator presses the shutter 211 of the shut-off valve 210 inwardly to allow high pressure air from air bottle 129 to pass through outlet 208 of the shut-off valve 210 and through stem 102 and tip 104 to produce full inflation of the balloon 105. The balloon fully inflated will assume a cup or dome shape in order to embrace the heart. This high pressure air will also flow into the expanded end 253 of pipe 252 and will bear against the head 262 of pin 261, driving pin 261 inward, against the urging of spring 264, to cause pin 261 to withdraw from opening 29 of the support case 2 and, hence, unlocking the stem member 100 from the support case 2 to permit the pumping operation. As shown in FIGS. 9 and 10, to perform the pumping operation, the operator alternately applies downward pressure to the handle 145 and releases such pressure. Since the stem member 100 is now unlocked from both the intermediate member 300 and from the support case 2, downward pressure on the handle 145 will be carried through the stem member 100 and will be applied through stem 102 to the balloon 105, causing the balloon 105 to be pressed against the heart 11 and, as pressure is applied to the balloon 105, to compress the heart 11 against the thoracic spine 13. Furthermore, since the handle 145 and tip 104 are both integral parts of the stem member 100, the operator receives tactile signals through the structure of the stem member 100 from which, with experience, he can determine the location of the balloon 105 with respect to the heart 11 and the direction and effect of the pressure applied thereto. If the balloon 105 during the pumping operation deflates accidentally, the pressure surrounding pin head 262 will fall allowing spring 264 to urge pin 261 to engage one of the openings 29 of support member 2, thus arresting the pumping operation. When the resuscitation operation has been completed, the operator unscrews and removes the air bottle 129, which allows the balloon 105 to deflate and permits the stem tip 104 and balloon 105 to be easily withdrawn from the chest cavity 110.

Figure 11:
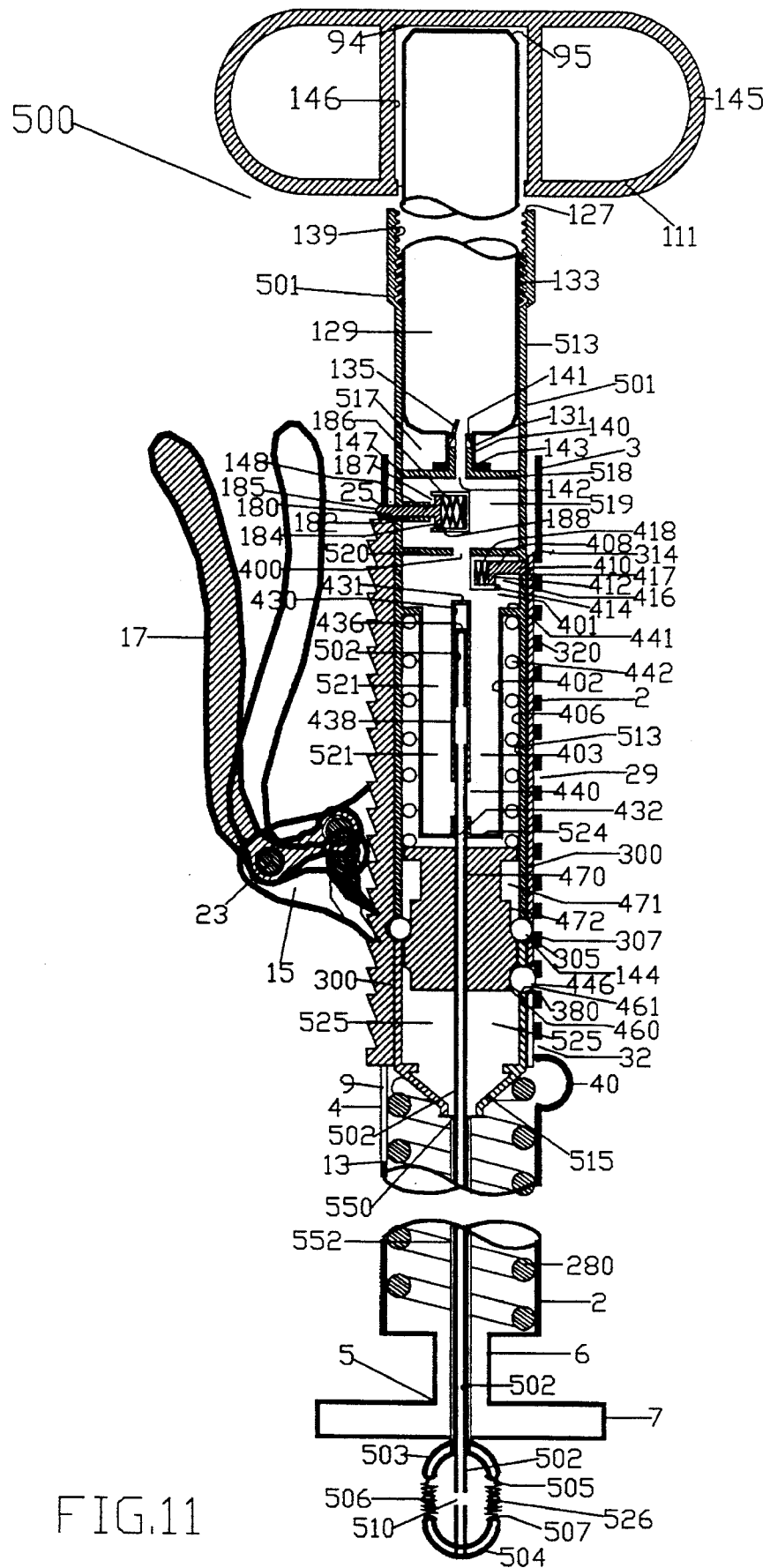
FIG. 11 is a vertical section of an alternative form of the cardiac pump.

FIG. 11 shows an alternative form, indicated generally at 500 of the cardiac pump 1 of FIGS. 1–10. The cardiac pump 500 of FIG. 11 differs from cardiac pump 1 of FIGS. 1–10 mainly in the structure and function of the stem unit generally indicated at 501, as it will be outlined below. The support case 2 and intermediate member 300 are basically the same as those of the cardiac pump 1 of FIGS. 1–10 and the same numbers have been used to identify the corresponding components thereof. The stem member 501 of the cardiac pump 500 is composed of three parts: handle 111, body 513 and stem 502 projecting from the distal end 515 of the body 513. Handle 111 is identical to handle of the cardiac pump 1 of FIGS. 1–10. The body 513 of stem member 501 of cardiac pump 500 is divided into four chambers: an upper chamber 517, a second chamber 519, a third chamber 521 and a lower chamber 525. The upper chamber 517 is identical to chamber 117 of FIGS. 1–10. As such it has an open upper end 127 to receive the compressed air bottle 129. The lower end of chamber 517 is defined by diaphragm 518, which is also identical to diaphragm 118 of the cardiac pump 1 of FIGS. 1–10. The second chamber 519 extends between diaphragm 518 and diaphragm 520, which is substantially identical to diaphragm 120 of the cardiac pump 1 of FIGS. 1–10, but has only a single central opening 400. Chamber 519 is basically the same as chamber 119 of FIGS. 1–10 and includes pin 180 and related structures as described in cardiac pump 100 of FIGS. 1–10. Shutter 190 of FIGS. 1–10 is no longer present in cardiac pump 500. Chamber 521 extends between diaphragm 520 and lower diaphragm 524 and is enclosed by side walls 402. Chamber 521 is composed of two adjoining compartments; upper compartment 401 and lower compartment 403. The upper end of side wall 402 is connected by annular flange 441 to the side walls 406 of body 513. Within the upper compartment 401, is a pin case 414 containing a pin 408, having a pin shaft 410 projecting laterally from a pin head 412 and urged outwardly of the pin case 414 by suitable means, such as spring 418, to cause the pin shaft 410 to project outwardly to engage in opening 417 of stem member 501. Pin shaft 410 is retained from further projecting outwardly by upper edge 314 of the wall of intermediate member 300. Pin case 414 also has a window 416 communicating with compartment 401. A pipe 430 extends axially through compartment 403 of chamber 521 and connects to opening 432, located centrally of diaphragm 524, and the closed upper end 436 of stem 502 is slideably mounted within and concentric with the pipe 430. Inner stem 502 extends downwardly through opening 432 of diaphragm 524 and continues, through lower chamber 525, and passes through opening 550 in the distal end 515 of chamber 525 to reach stem tip 526 continuing in its convex apex 504 of stem tip 526. Inner stem 502 is encircled by outer stem 552 which projects from distal end 515 of chamber 525 of stem member 501 and exits through opening 31 of flat base 7 of support case 2 to continue in tip base 503 of tip 526. Inner stem 502 is slideably mounted within outer stem 552. Adjacent its upper end 436, stem 502 is provided with windows 438, while pipe 430 is formed with windows 440, which are normally out of alignment with the windows 438 of stem 502, but which, when aligned, as described hereinafter, allow fluid flow between compartment 403 and the interior of the stem 502. A spring 442 is located between the side wall 402 of compartment 403 and the side wall 406 of body 513, between flange 441 and the upper surface of piston 470. In passing through chamber 525, stem 502 extends axially through piston 470 and is secured to the piston 470 for movement therewith. Piston 470 is formed with an annular recess 471, having an annular extension 472. In the rest position, balls 305 are seated in extension 472 of piston 470 and project through opening 144 in wall 406 of the body 513 of the stem member 501 to seat in receptacle 307 of the intermediate member 300 to releasably lock the stem member 501 to the intermediate member 300. Also, ball 446 seats in an annular recess 460, at the lower end of piston 470, and projects through opening 461 in wall 406 of the body 513 of stem member 501 to seat in window 380 of the intermediate member 300 to prevent downward movement of the piston 470 and, hence, of stem 502. The stem tip 526 has the same overall shape of stem tip 104 of the cardiac pump 1 of FIGS. 1–10, however it is structurally and functionally different. Stem tip 526 is composed of tip base 503 which, as outlined above, is in continuity with outer stem 552 and a convex apex 504 which, as outlined above, is in continuity with inner stem 502. Between edges 505 of tip base 503 and edge 507 of convex apex 504 is contained folded expandable member such as balloon 506. Also, the lower end of inner stem 502 is formed with windows 510 which allow air to pass out of inner stem 502 to inflate the balloon 506, when appropriate. The support case 2 is formed with a receptacle 473, located adjacent the lower end 550 of the body 513 of the stem member 501 when the cardiac pump 500 is in the rest position, for receiving the ball 446, as described hereinafter.

In operation, the cardiac pump 500 of FIG. 11 is placed within skin incision 109, in the same manner as cardiac pump 1 of FIGS. 1–10, with stem tip 526 partially buried under the patient's skin. Compressed air bottle 129 is, then, screwed into chamber 517, causing penetration of seal 135 by needle tip 141 of needle 140, and allowing air to pass through opening 400 into chambers 519 and 521. The air pressure in chamber 519 will result in lateral withdrawal of pin 180, against the urging of spring 186, unlocking the stem member 501 and intermediate member 300 for downward movement with respect to the support case 2, due to the action of lever 17 and the double rack 301, in the same manner as described above with respect to cardiac pump 1 of FIGS. 1–10.

When lever 17 and the double rack 301 have advanced the stem member 501 and intermediate member 300 a predetermined distance, preferably approximately ½ centimeter, ball 446 will enter receptacle 40 of the support case 2, releasing piston 470 for downward movement by spring 442. However, such downward movement is prevented, at this time, since the tip apex 504 is engaging the inextensible structure of the chest wall 107 and, thus, serves to prevent downward movement of stem 502 and piston 470. Continued operation of lever 17 on the double rack 301 will, eventually, cause the stem tip 526 to penetrate into the chest cavity 110, whereupon downward movement of the stem tip 526 is no longer impeded by the structure of the chest wall 107. The instant such penetration of the chest cavity 110 occurs, spring 442 will drive piston 470 and stem 502 downward, causing windows 438 of stem 502 to align with windows 440 of pipe 430 and allowing air to pass from chamber 521, through stem 502 and windows 510 to inflate the balloon 506. The downward movement of piston 470 also allows balls 305 to be moved out of extension 472 of piston 470, to enter recess 471 of piston 470 and to disengage from receptacle 307 of the intermediate member 300 and, thus, to unlock the stem member 501 from the intermediate member 300. However, prior to full inflation of the balloon 506, pin shaft 410 of pin 408 will be urged by spring 418 to project through longitudinal slit above edge 314 of the intermediate member 300 into one of the openings 29 of the support case 2 to prevent forward movement of the stem member 501. When the balloon 506 is fully inflated, the air pressure in chamber 521 will rise, causing pin head 412 to drive pin 408 inwardly, against the urging of spring 418, withdrawing pin shaft 410 through slit above edge 314 of the intermediate member 300, out of opening 29 of support case 2, to fully release the stem member 501 for the pumping operation, which is performed in the manner described above with respect to the cardiac pump 1 of FIGS. 1–10. In case balloon 506 during the pumping operation deflates accidentally, pressure surrounding pin head 412 of pin 408 will fall, allowing spring 418 to urge pin 408 outwardly to engage one of the openings 29 of support member 2. When the resuscitation operation has been completed, the operator unscrews and removes the air bottle 129, which allows the balloon 506 to deflate and permits the stem tip 526 and balloon 506 to be easily withdrawn from the chest cavity 110.

Figure 12:
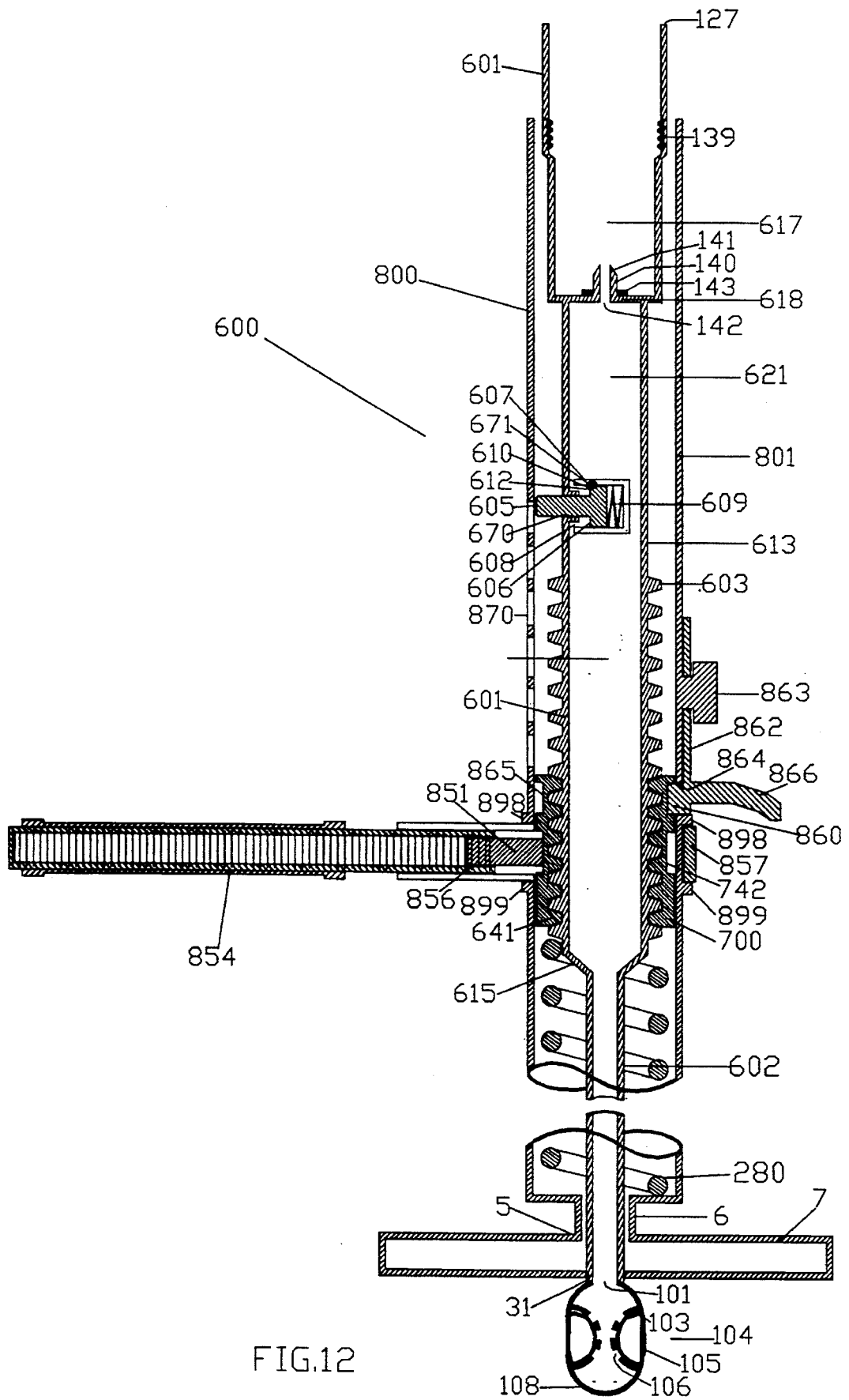
FIG. 12 is a vertical section of another alternative form of the cardiac pump.
Figure 14:
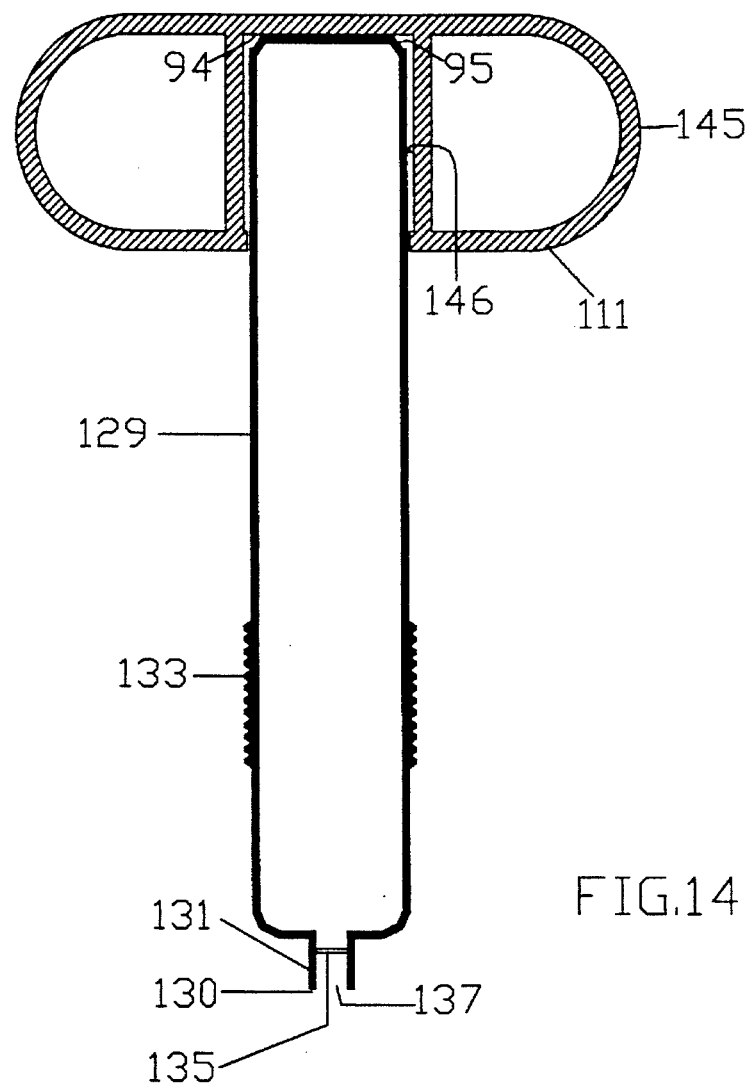
FIG. 14 shows a top view of the lever of the device of FIG. 12.
Figure 13:
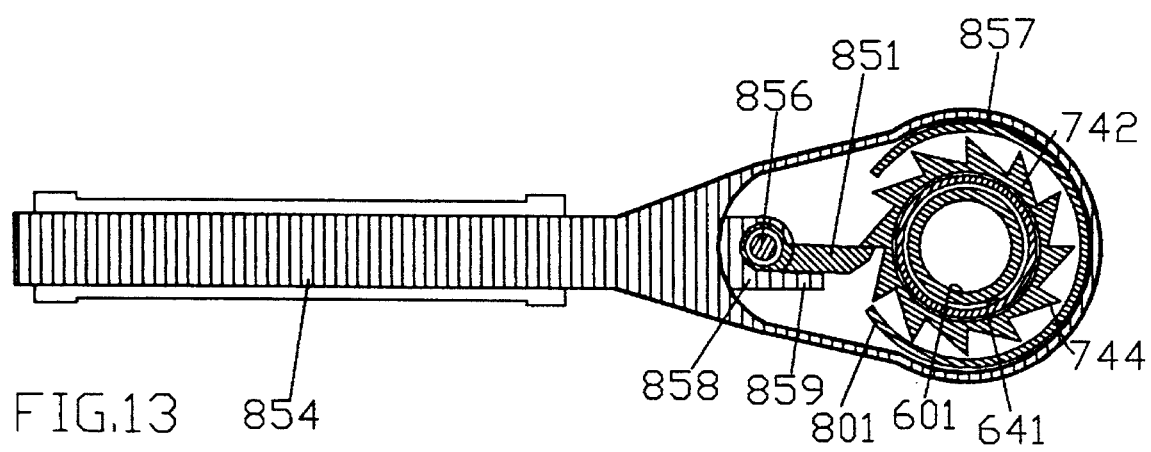
FIG. 13 is a vertical section through the handle portion of the cardiac pump of FIG. 12.

FIGS. 12, 13 and 14 show a further alternative form, indicated generally at 600, of the cardiac pump 1 of FIGS. 1–10, having a support case 800, which is similar to the support case 2 of the cardiac pump 1 of FIGS. 1–10; a stem member 601, and an intermediate member 700. The stem member 601 as shown in FIG. 13, comprises a handle 111, mounted atop a compressed air bottle 129, which is threadedly attached to the upper end of a generally cylindrical body 613 of stem member 601. The body 613 is divided into upper chamber 617 and lower chamber 621. Chamber 617 is identical to chamber 517 of the cardiac pump 500 of FIG. 11. Diaphragm 618 separates chambers 617 and 621 and has a central opening 142, surrounded by hollow needle 140 which has pointed end 141 and is identical with hollow needle 140 of the cardiac pump 1 of FIGS. 1–10. Chamber 621 extends between diaphragm 618 and the distal end 615 of the body 613, while hollow stem 602 communicates with end 615 of the body 613 and projects through the base 7 of the support case 800 to communicate with stem tip 104, which is identical with the stem tip 104 of the cardiac pump 1 of FIGS. 1–10. Within chamber 621 is a pin case 607 having a window 608 and containing a pin 605 which projects through opening 670 of the wall of body 613 and is formed with a head 606 that is normally urged laterally outward by a spring 609 contained within the pin case 607. However, the action of spring 609 causes the pin head 606 to bear against ball 610, which is seated in receptacle 671 of the pin case 607 and prevents outward movement of the pin 605 until the ball 610 is released as described hereinafter. The exterior of the body 613 is provided with a male threaded portion 603 which mates with the female threaded portion 641 of the intermediate member 700. The intermediate member 700 is interposed between the stem member 601 and the support case 800 and is of generally cylindrical shape, with the female threaded portion 641 located approximately midway of the length of the intermediate member 700, and has an annular rack 742 extending about the exterior of the middle of the intermediate member 700, provided with a plurality of outwardly projecting teeth 744. The support case 800 has a generally hollow, cylindrical body 801 encircling the intermediate member 700 and the stem member 601 and the upper portion of the body 801 of support case 800 is provided with a vertical row of small openings 870 for receiving the pin 605 of the stem member 601. Lever 854 encircles with its expanded head 857 support member 800 at its midportion and is held in that midportion by the presence of two annular rails 898 and 899. Lever 854 carries a dog support 858 to which a dog 851 is pivotally secured via a pin 856 and is provided with dog arrest 859 for dog 851. Dog 851 projects through opening 853 of support member 800 and reachs for ratcheting engagement the teeth 744 of the annular rack 742 mounted on the intermediate member 700. The support case 800 also carries a pin 860 mounted externally of support member 800 by a flexible arm 862, which is secured to support member 800 by a button 863 and extends downwardly from the button 863 to allow the pin 860 to project through opening 864 of support case 800 to engage annular recess 865 of the intermediate member 700. A handle 866 projects outwardly from the pin 860 to permit manual actuation of the pin 860.

In use, the cardiac pump 600 of FIGS. 12, 13 and 14 and 10 is placed on the patient's chest either on the anterior chest wall in the fourth or fifth intercostal space or in the subxyphoideal region within skin incision 109, in the manner described above with respect to the cardiac pump 1 of FIGS. 1–10, with the stem tip 104 partially buried within the chest wall structure 107. The operator then ratchets the lever 854 laterally, while keeping the base 7 of the support case 601 pressing steadily against the patient's chest. This action causes dog 851 to drive the teeth 744 on rack 742 to rotate the intermediate member 700. Since the operator is preventing rotation of the stem member 800, by his grip on handle 145, and since intermediate member 700 is prevented from advancing, by pin 860 projecting through opening 864 and engaging annular recess 865 of the intermediate member 700, the rotation of the intermediate member 700 will cause threads 641 to interact with threads 603 of the stem member 600 to force the stem member 601 to advance the stem tip 104 through the chest wall structure 107 until the stem tip 104 penetrates the chest cavity 110. The gradual and controlled slow advancement will finally result in penetration of the stem tip 104 into the chest cavity 110. Once the passage of a relatively broad stem end 104 is completed and relatively narrow stem 602 is engaged in the chest hole formed by stem end 104, the operator will have an immediate tactile signal of front and side clearance of the stem 602 in the hole formed in the chest wall. Upon receipt of this signal, the operator will cease to actuate the lever 854 and will screw in the air bottle 129, causing needle point 141 of needle 140 to rupture the seal 135 and allowing compressed air from the air bottle 129 to inflate the balloon 105. As the balloon 105 reaches full inflation, the air pressure within the stem member 601 will increase and will drive pin 605 inward, against the action of spring 609, allowing ball 610 to be released from receptacle 612 thus freeing pin 605. The operator will then unlock the intermediate member 700 from the support case 800 by pulling handle 864 of pin 860 to disengage pin 860 from the annular recess 865 of the intermediate member 700 to permit the operator to commence the cardiac pumping by alternately pressing and releasing the handle bar 145 of handle 111. If the balloon 105 should become deflated during the pumping operation, the air pressure within the stem member 601 will fall, allowing spring 609 to urge freed pin 605 laterally outward to project through one of the openings 870 of the support case 800 to lock the stem member 601 to the support case 800 and, hence, to prevent further pumping and possible damage to the heart 69.

Figure 15:
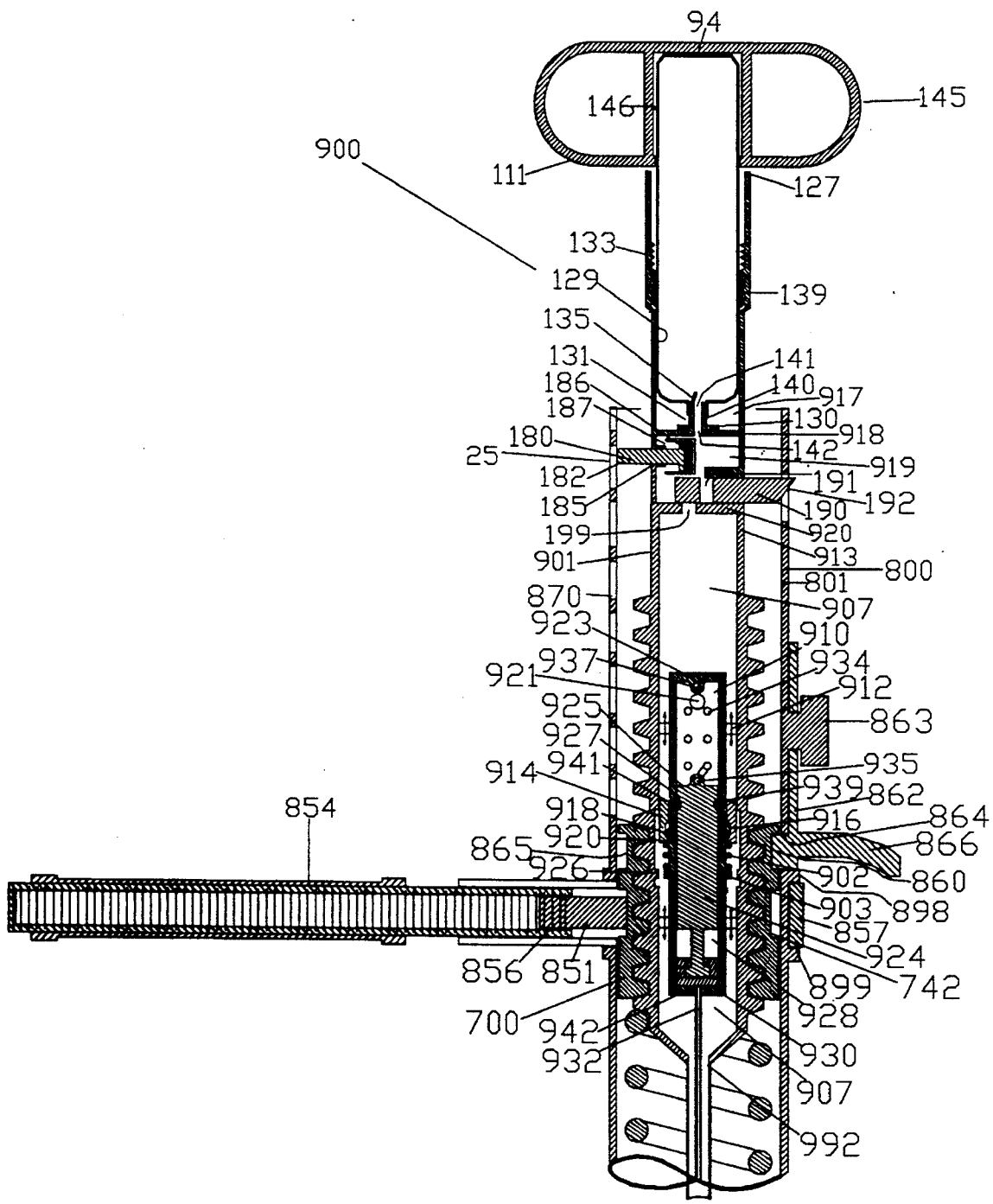
FIG. 15 is a vertical section of a further alternative form of the cardiac pump.
Figure 15:
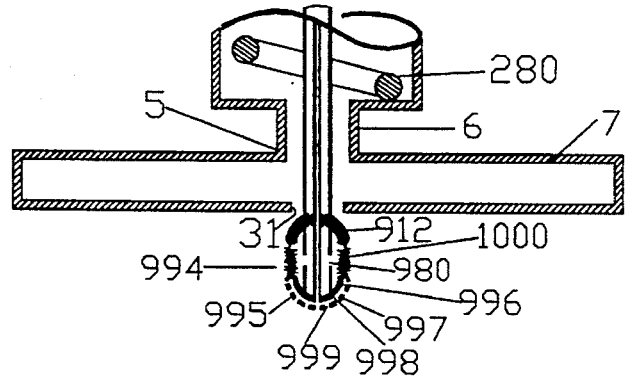
Figure 16:
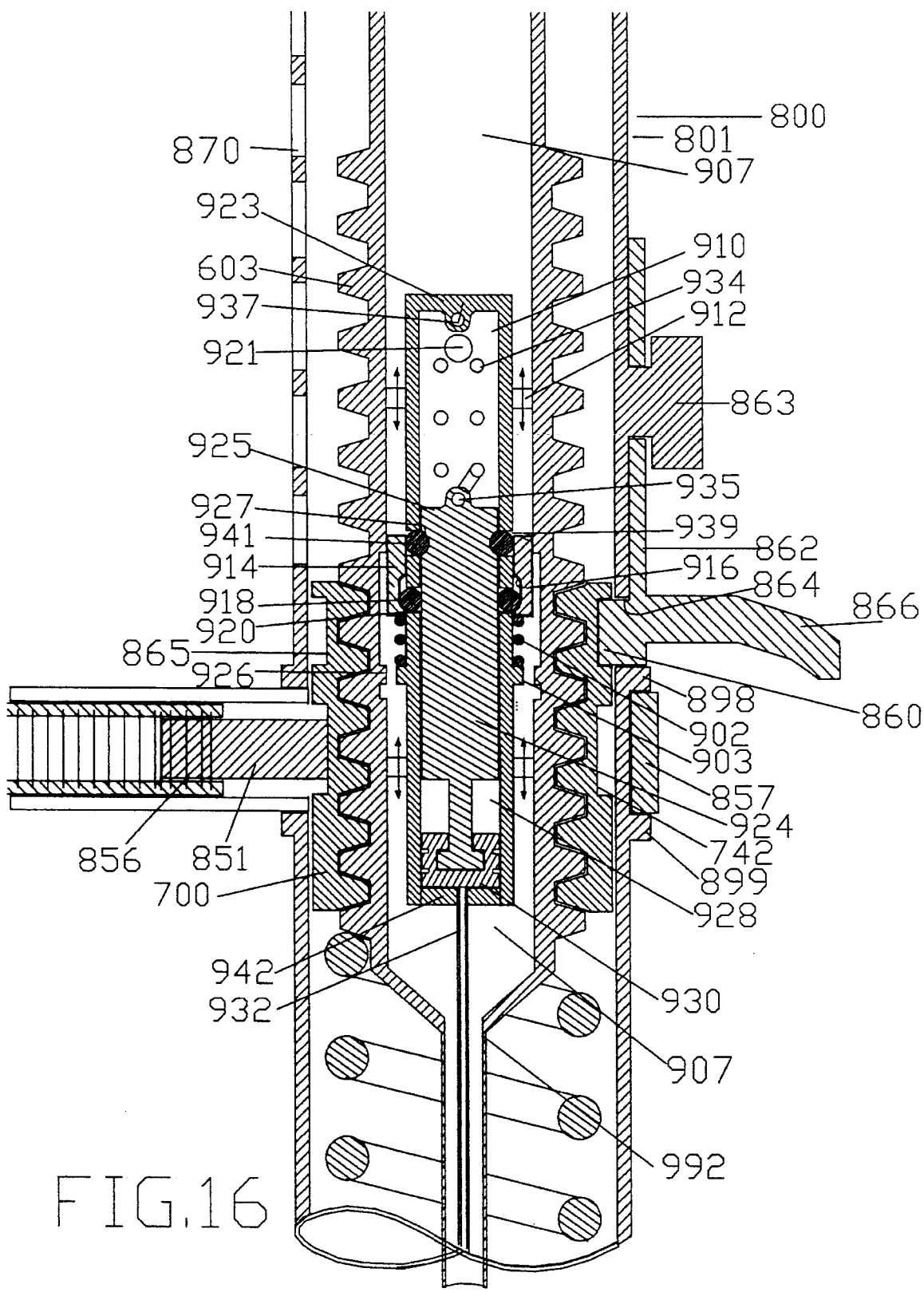
FIG. 16 is an enlarged detail view of the midportion of the cardiac pump of FIG. 15.
Figure 17:
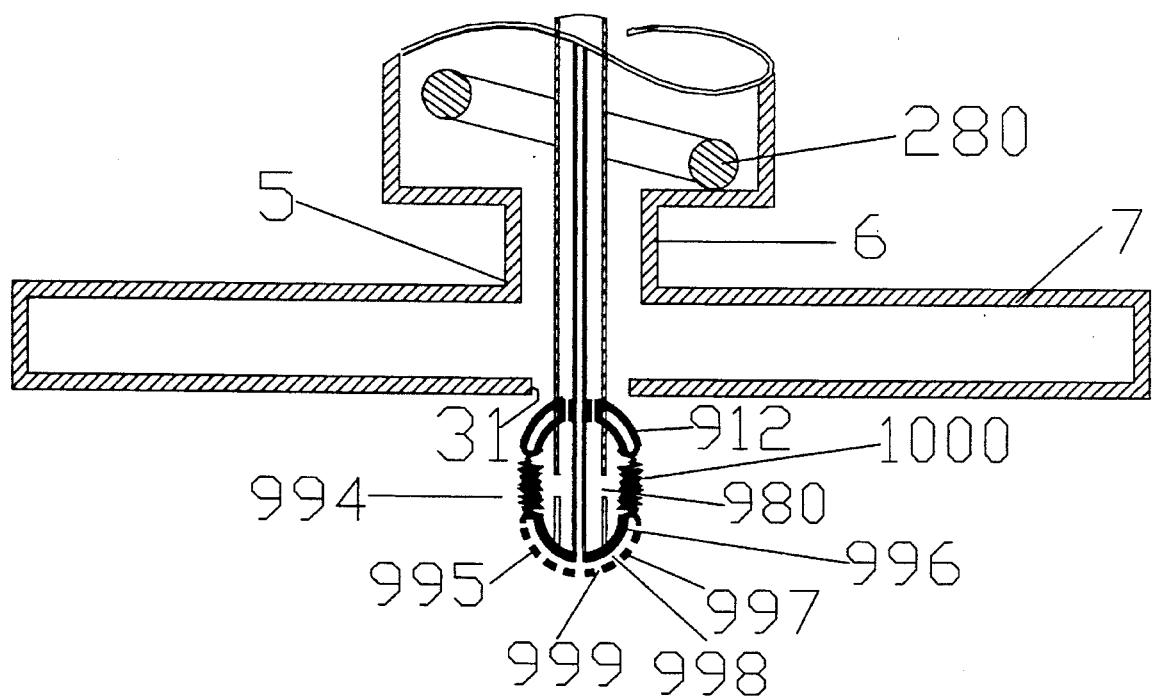
FIG. 17 is an enlarged vertical section through the stem tip of the cardiac pump of FIG. 15.

FIGS. 15, 16 and 17 show another alternative form, indicated generally at 900, of the cardiac pump 1 of FIGS. 1–10. The stem member 901 of cardiac pump 900 is different from those previously described, although the support case 800 and intermediate member 700 are identical with those of the cardiac pump 600 of FIGS. 12–14. The stem member 901 is composed of handle 111, body 913 and stem 992, having a stem tip 994. Body 913 of stem member 901 of pump 900 is divided into three chambers: upper chamber 917, central chamber 919 and lower chamber 907. Upper chamber 917 is identical to chamber 517 of the cardiac pump 500 of FIG. 11. Diaphragm 918 separates chambers 917 and 919 and has a central opening 142, surrounded by hollow needle 140 with pointed end 141, identical to the one described in the embodiment of FIGS. 1–10. Chamber 919 contains a pin 180 and a shutter 190, which are identical to the corresponding components of the cardiac pump 1 of FIGS. 1–10, and has a diaphragm 920 formed with a central opening 199, which is normally blocked by shutter 190, and separating the central chamber 919 from the lower chamber 907. Lower chamber 907 contain a cylindrical vacuum chamber 910, which is mounted axially within chamber 907 by a pair of support arms 912 extending between the vacuum chamber 910 and the body 913 of the stem member 901, as best seen in FIG. 16. A sealing cylinder 914 encircles the middle of the vacuum chamber 910 and is normally urged upward by spring 902, bearing against flange 903, which projects radially outward from the vacuum chamber 910. Another flange 926 projects radially inward from the body 913 of the stem member 901 to limit downward movement of the sealing cylinder 914. The sealing cylinder 914 is formed with an inwardly facing annular recess 916. In the rest position of the pump 900, balls 918 are seated in recess 916 and in windows 920 of vacuum chamber 910. The locking piston 924 is axially slidable within the vacuum chamber 910 and carries a sealing cap 930 at its lower end with an annular recess 928 formed immediately above the sealing cap 930. Lower end of chamber 907 of stem member 913 projects in outer stem 992 which slides through hole 31 of flat base 7 of support case 2 to reach stem end 994 firmly supporting both hollow convex apex 995 and solid base 912 of stem end 994. Inner stem 932 projects from distal end 942 of vacuum chamber 910 and extends concentrically inside hollow outer stem 992, downward to reach and communicate with hollow convex apex 995.

Hollow convex apex 995 has a solid inner wall 996 and an outer wall 997 separated by a space 998 therebetween. Inner stem 932 penetrates inner wall 996 and communicates the space 998 with the lower end 942 of the vacuum chamber 910 within the body 913 of the stem member 901. The outer wall 997 is formed with a plurality of openings 999. Finally, a balloon 1000 is mounted between the adjacent edges of the concave base 912 and the convex apex 995 and windows 980 are formed in the lower portion of outer stem 992 communicating the interior of the balloon 105 with the interior of body 913 of the stem member 901.

In use, the compressed air bottle 129 is screwed into upper chamber 917, causing needle point 141 of needle 140 to rupture the seal 135 and allowing compressed air from the air bottle 129 to enter chamber 919 and to displace pin 180 inward, unlocking the stem member 901 from the support case 800. The operator then ratchets lever 854, as described for cardiac pump 600 of FIG.12–14, causing advancement of the stem member 901 with respect to the support case 800, until shutter 190 is displaced inward by body 801 of the support case 800, causing air to pass through opening 199 into chamber 907 surrounding the vacuum chamber 910. This air pressure drives the sealing cylinder 914 downward, against the urging of spring 902, and allowing balls 941 to move out of the annular recess 927 to unlock piston 924 from the vacuum chamber 910. However, spring 934 is unable, at this time, to move piston 924 upward, since such action will cause the sealing cap 930, carried by the lower end of piston 924 to create a vacuum within the vacuum chamber 910 below piston 924, since the chest wall structure 107 prevents air from entering stem tip 994 and passing through inner stem 932 into the vacuum chamber 910. This vacuum will resist the upward urging of spring 934. However, as soon as the stem tip 994 enters the chest cavity 110, air from within the chest cavity 110 can enter stem tip 994 and flow through inner stem 932 to relieve this vacuum and to allow spring 934 to move piston 924 to its upward position, wherein balls 918 can pass into the annular recess 928, adjacent the lower end of piston 924, to unlock piston 924 from the sealing cylinder 914. Spring 902 then drives the sealing cylinder 914 to its upward position, which allows the compressed air in chamber 907 to bypass the sealing cylinder 914 and to flow through outer stem 992 and windows 980 of stem end 994 to inflate the balloon 1000. The operator may then apply periodic pressure to the handle bar 145 to perform the pumping operation. If the balloon 1000 should accidentally deflate during the pumping operation, the air pressure within the stem member 901 will fall, allowing spring 186 to urge pin 180 laterally outward to project through one of the openings 870 of the support case 800 to lock the stem member 901 to the support case 800 and, hence, to prevent further pumping and possible damage to the heart 69.

Obviously, numerous other variations and modifications can be made without departing from the spirit of the present invention. Therefore, it should be clearly understood that the forms of the present invention described above and shown in the figures of the accompanying drawing are illustrative only and are not intended to limit the scope of the present invention.

What is claimed is:

1. A cardiac pump comprising:
an expandable member placeable inside a chest cavity adjacent to a heart, and
means for periodically displacing said expandable member toward the heart and away from the heart by applying and releasing mechanical pressure to said expandable member, said expandable member periodically applying and releasing said mechanical pressure to an exterior surface of the heart for compressing and decompressing the heart to effect pumping of the heart.

2. The cardiac pump of claim 1 wherein:
said means for periodically displacing said expandable member comprises:
a stem member carrying said expandable member, said stem member being sufficiently rigid to transmit said applied pressure to said expandable member.

3. The cardiac pump of claim 2 wherein:
said stem member is hollow and connected at one end to said expandable member.

4. The cardiac pump of claim 3 further comprising:
means for expanding said expandable member through said hollow stem.

5. The cardiac pump of claim 4 wherein: said expanding means is pneumatic.

6. The cardiac pump of claim 4 wherein: said expanding means is hydraulic.

7. The cardiac pump of claim 1 wherein:
said expandable member comprises a balloon.

8. The cardiac pump of claim 7 wherein:
said balloon is dome-shaped.

9. The cardiac pump of claim 2 further comprising:
means for passing said expandable member in a contracted state through a wall delimiting the chest cavity.

10. The cardiac pump of claim 2 further comprising:
means for placing said expandable member within the chest cavity adjacent to the heart.

11. The Cardiac pump of claim 2 further comprising:
means for penetration through a wall delimiting the chest cavity of a portion of said stem member.

12. The cardiac pump of claim 11 wherein: said means for penetration comprises:
means for preventing punctures and lacerations of intrathoracic organs.

13. The cardiac pump of claim 11 wherein:
said means for penetration includes:
a blunt end of said stem member.

14. The cardiac pump of claim 9 wherein:
said means for passing said expandable member through said wall delimiting the chest cavity includes:
means for expanding said expandable member upon entry of said expandable member within the chest cavity.

15. The cardiac pump of claim 14 wherein:
said means for expanding said expandable member are automatically actuated in response to entry of said expandable member within the chest cavity.

16. The cardiac pump of claim 9 wherein:
said means for passing said expandable member through said wall delimiting the chest cavity includes: means for advancement.

17. The cardiac pump of claim 16 wherein:
said means for advancement comprises:
means for gradual advancement.

18. The cardiac pump of claim 16 wherein:
said means for gradual advancement comprises:
   a toothed rack anchored to said stem member and
   a lever acting longitudinally upon said toothed rack.

19. The cardiac pump of claim 16 wherein:
said means for gradual advancement comprises:
   an annular rack with a screw thread mating a corresponding screw thread formed in said stem member and
   a lever rotating said annular rack.

20. The cardiac pump of claim 16 further comprises:
means for disabling said means for advancement upon entry into the chest cavity of said expandable member.

21. The cardiac pump of claim 16 further comprises:
means for arresting said means for advancement upon entry into the chest cavity of said expandable member.

22. The cardiac pump of claim 2 further comprises:
means for sensing penetration into the chest cavity.

23. The cardiac pump of claim 22 wherein: said means for sensing penetration includes:
   means for placing under expanding pressure said expandable member, not allowed to expand under said expanding pressure during passage of said expandable member through a wall of the chest by resistance of layers of said chest wall, and permitted to expand upon entry into the chest cavity and, by expanding upon entry into the chest cavity, signaling penetration into the chest cavity.

24. The cardiac pump of claim 22 wherein: said means for sensing penetration includes:
   a convex apex slideably mounted on a stem end of said stem member, said convex apex being urged forwardly by resilient means in respect to said stem member, said convex apex being (which is) constrained during its passage through the chest wall by underlying layers, and being permitted to (advances) advance in respect to said stem member upon entry of the chest cavity, and, by advancing, signaling penetration into the chest cavity.

25. The cardiac pump of claim 22 wherein: said means for sensing penetration includes:
   an enlarged stem end which, upon penetration into the chest cavity, allows an operator to tactually sense entry into the chest cavity by sudden fall of resistance to front and side movement of said stem end.

26. The cardiac pump of claim 22 wherein: said means for sensing penetration includes:
   a perforated stem end communicating with a chamber through a hollow stem,
   a vacuum within said chamber, said vacuum being (which is) retained during passage of said perforated stem end (within) through tissues of said chest wall (of the chest cavity) due to (the) sealing of said perforated stem end by said (wall) tissues, and said vacuum (is relieved) vanishing upon entry of said perforated stem end into the chest cavity by unsealing of the perforated stem end due to absence of said tissues as a result of the entry of said perforated stem end into said chest cavity, said vanishing of the vacuum signaling penetration into the chest cavity (entry of air into the vacuum chamber through said perforated stem end).

27. The cardiac pump of claim 1 further comprising:
a support case having a flat base
a stem member slideable within said support case having a stem end projecting below said base, and
an intermediate member interposed between said stem member and said support case,
means for advancing said stem member with respect to said support case to cause said stem end to penetrate through structures of a wall of said chest cavity
said expandable member being carried by said stem end of said stem member.

28. The cardiac pump of claim 27 further comprising:
locking means releasably locking said stem member to said intermediate member to prevent inadvertent advancing of said stem member, and
means responsive to entry of said stem end into a chest cavity for releasing said locking means to permit pumping movement of said stem member.

29. The cardiac pump of claim 27 further comprising:
means for expanding said expandable member upon entry of said stem end into said chest cavity.

30. The cardiac pump of claim 2, further comprises:
means for arresting forward displacement of said stem member upon accidental contraction of said expandable member within the chest cavity.

31. The method of Cardiac Resuscitation comprising the steps of:
inserting an expandable member in a contracted state into a patient chest cavity adjacent to the heart,
expanding said expandable member, and,
periodically displacing said member forward and backward by applying and releasing mechanical pressure to said expandable member, said expandable member applying and releasing mechanical pressure upon en exterior surface of the heart so as to compress and decompress the heart against the thoracic spine.

32. The method of claim 31 wherein:
said step of inserting of said expandable member is carried out on the 4th intercostal space.

33. The method of claim 31 wherein:
said step of inserting of said expandable member is carried out on the 5th intercostal space.

34. The method of claim 31 wherein:
said step of inserting of said expandable member is carried out on the subxyphoid region.

35. A cardiac pump comprising:
an expandable member carried at a distal end of a stem member, said stem member end being placeable inside a chest cavity adjacent to a heart by
means for blunt dissection of tissues of a chest wall delimiting said chest cavity without puncture or laceration of the heart, coronary vessels or surrounding organs and tissues, and
means for periodically applying pressure upon an exterior surface of the heart via said expandable member for compressing and decompressing the heart to effect pumping of the heart.

36. The cardiac pump of claim 35 further comprising:
means for passing said expandable member in a contracted state through said wall delimiting said chest cavity.

37. The cardiac pump of claim 36 wherein:
said means for passing said expandable member within the chest cavity adjacent to the heart comprises:
   an inserting mechanism for controlled insertion and direction of the stem member end carrying said expandable member into the chest cavity and in front of the heart.

38. The Cardiac pump of claim 37 further comprising:

means for (penetration) penetrating said stem member through a wall delimiting the chest cavity (of a portion of said stem member) with automatic arrest of stem member advancement once the stem end has entered the chest cavity.

39. The cardiac pump of claim 38 wherein:

said means for penetration comprises:
means for preventing punctures and lacerations of intra thoracic organs.

40. The cardiac pump of claim 38 wherein:

said end of said stem member is blunt.

41. A cardiac pump comprising:

a stem member having a blunt distal end, means for advancing said stem member toward a chest cavity through a chest wall to penetrate through structures of said chest wall of a patient, an expandable member carried by said stem member distal end, and means for periodically transferring a pressure applied to a proximal end of said stem member upon an exterior surface of the heart to effect pumping of the heart, said stem member being sufficiently rigid to transfer said pressure upon said exterior surface of the heart.

42. The cardiac pump of claim 41 further comprising:

a support case having a flat base, said stem member being slideable within said support case with said blunt stem end projecting below said base, an intermediate member interposed between said stem member and said support case, said means for advancing said stem member advances said stem member with respect to said support case to cause said stem end to penetrate through the chest wall structure of the patient, 43. The cardiac pump of claim 42 further comprising:

locking means releasably locking said stem member to said intermediate member to prevent inadvertent advancing of said stem member.

44. The cardiac pump of claim 42 further comprising:

means for expanding said expandable member upon entry of said blunt stem end into said chest cavity.

45. A method of Cardiac Resuscitation comprising the steps of:

applying a rigid stem member mounted within a case to a chest cavity;

advancing the stem member relative to the case, said stem member having a blunt distal end carrying an expandable member in a contracted state into a patient chest cavity adjacent to the exterior surface of the heart and pumping the heart by said expandable member.

46. A cardiac pump comprising:

an expandable member placeable inside a chest cavity adjacent to a heart, means for inserting said expandable member into the chest cavity through a chest wall delimiting said chest cavity without puncturing or lacerating the heart, coronary vessels or surrounding organs and tissues and means for periodically applying pressure upon an exterior surface of the heart via said expandable member for compressing and decompressing the heart to effect pumping of the heart.

47. The cardiac pump of claim 46 wherein:

said means for inserting said expandable member into the chest cavity through said wall delimiting the chest cavity includes:
means for expanding said expandable member upon entry of said expandable member within the chest cavity.

48. The cardiac pump of claim 47 wherein:

said means for expanding said expandable member are automatically actuated in response to entry of said expandable member within the chest cavity.

49. The cardiac pump of claim 46 wherein:

said means for inserting said expandable member into the chest cavity through said chest wall delimiting the chest cavity includes:
means for advancement.

50. The cardiac pump of claim 49 wherein:

said means for advancement comprises:
means for gradual advancement.

51. The cardiac pump of claim 50 wherein:

said means for gradual advancement comprises:
a stem member
a toothed rack anchored to said stem member and
a lever acting longitudinally upon said toothed rack.

52. The cardiac pump of claim 50 wherein:

said means for gradual advancement comprises:
a stem member
an annular rack with a screw thread mating a corresponding screw thread formed in said stem member and
a lever rotating said annular rack.

53. The cardiac pump of claim 49 further comprises:

means for disabling said means for advancement upon entry into the chest cavity of said expandable member.

54. The cardiac pump of claim 49 further comprises:

means for arresting said means for advancement upon entry into the chest cavity of said expandable member.

55. The cardiac pump of claim 46 wherein:

said means for inserting said expandable member into the chest cavity through the chest wall comprises:
means for sensing penetration into the chest cavity.

56. The cardiac pump of claim 55 wherein said means for sensing penetration includes:

means for placing under expanding pressure said expandable member, not allowed to expand under said expanding pressure during its passage through the wall of the chest by the resistance of the chest wall structures, and permitted to expand upon entry into the chest cavity and, by expanding upon entry into the chest cavity, signaling penetration into the chest cavity.

57. The cardiac pump of claim 55, wherein:

said means for sensing penetration includes:
a convex apex slideably mounted on a stem end of said stem member, said convex apex being urged forwardly by resilient means in respect to said stem member, said convex apex being (which is) constrained during its passage through the chest wall by underlying layers, and being permitted to (advances) advance in respect to said stem member upon entry into the chest cavity, and, by advancing, signaling penetration into the chest cavity.

58. The cardiac pump of claim 55 wherein:

said means for sensing penetration includes:
a stem member having an enlarged stem end, said stem end carrying said expandable member, wherein said enlarged stem end, upon penetration of said stem end into the chest cavity, allows an operator to tactually sense entry into the chest cavity by sudden fall of resistance to front and side movement of said stem end.

59. The cardiac pump of claim 55 wherein:

said means for sensing penetration includes:

a perforated stem end communicating with a chamber through a hollow stem, a vacuum within said chamber, said vacuum being (which is) retained during passage of said perforated stem end (within) through tissues of said chest wall (of the chest cavity) due to sealing of said perforated stem end by said tissues, and said vacuum (is relieved) vanishing upon entry of said perforated stem end into the chest cavity by unsealing of the perforated stem end due to absence of said tissues as a result of the entry of said perforated stem end into said chest cavity, said vanishing of the vacuum signaling penetration into the chest cavity (entry of air into the vacuum chamber through said perforated stem end).

60. A cannular surgical device for passing through a slightly incised body wall of a body to a limited extent into a body cavity for gaining access to organs, glands, tissues or vessels without puncture or laceration of the organs, glands, tissues or vessels, comprising:

a) a support case having a base adaptable for placement on the body adjacent the body wall to be passed;

b) a stem slideably mounted within the case having a blunt end extensibly projectable from the base, the blunt end being adapted to pass into the body incision carrying a means to operate on a particular organ, gland, tissue or vessel;

c) means for advancing the stem in the case and advancing the blunt end through the body wall and to a limited extent into the body cavity adjacent the particular organ, gland, tissue or vessel; and d) a handle connected to the stem opposite the base and extending from the case for manipulating the stem end within the body cavity.

61. The device of claim 60 further comprising:

a) an intermediate member interposed between the stem and the support case;

b) locking means for releasably locking the stem to the intermediate member to prevent inadvertent advancing of the stem and stem end.

62. A cardiac pump placeable on a body with portions passable through a slightly incised chest wall to gain access to a heart within a chest cavity in need of massage without radical open chest surgery and without puncture or laceration of the heart or adjacent organs, glands, tissues or vessels, comprising:

a) a support case having a base adaptable for placement on the body adjacent the chest wall to be passed;

b) a stem slideably mounted within the case having a blunt end extensibly projectable from the base, the blunt end being adapted to pass in the body incision carrying a compressed expandable member to operate on the heart; and c) means for advancing the stem in the case and advancing the blunt end through the chest wall and to a limited extent into the chest cavity adjacent the heart, after which the expandable member is adapted to expand for massaging the heart within the chest cavity.

63. A method for percutaneous cardiopulmonary resuscitation of an arrested heart below a chest wall within a chest cavity of a person, comprising:

a) placing a base of a support case on the chest wall above the heart of a reclined person;

b) making a measured partial incision into the chest wall above the heart of a reclined person in need of heart massage;

c) placing the blunt end of a stem carrying an expandable member into the incision, the stem being supported on the chest by a rigid support case resting on the chest wall;

d) advancing the stem within the case and the blunt stem end further into the incision and through the chest wall;

e) expanding the expandable member within the chest cavity adjacent the heart; and f) massaging the heart with the expandable member from outside the chest cavity.

* * * * *